US006566134B2

(12) United States Patent
Bringe

(10) Patent No.: US 6,566,134 B2
(45) Date of Patent: May 20, 2003

(54) HIGH BETA-CONGLYCININ PRODUCTS AND THEIR USE

(75) Inventor: Neal A. Bringe, Saint Charles, MO (US)

(73) Assignee: Monsanto Company, St. Louis, MO (US)

( * ) Notice: Subject to any disclaimer, the term of this patent is extended or adjusted under 35 U.S.C. 154(b) by 0 days.

(21) Appl. No.: 09/742,962

(22) Filed: Dec. 20, 2000

(65) Prior Publication Data

US 2001/0024677 A1 Sep. 27, 2001

Related U.S. Application Data

(60) Division of application No. 09/167,810, filed on Oct. 7, 1998, now Pat. No. 6,171,640, which is a continuation-in-part of application No. PCT/US98/06579, filed on Apr. 3, 1998.
(60) Provisional application No. 60/042,643, filed on Apr. 4, 1997.

(51) Int. Cl.[7] .............................. C12N 3/00; A23J 1/00; A23J 3/00; A23J 3/14; A23J 3/16
(52) U.S. Cl. ...................... 435/410; 435/415; 435/814; 435/815; 435/816; 530/412; 530/418
(58) Field of Search ................................. 530/412, 418; 435/410, 415, 814, 815, 816

(56) References Cited

U.S. PATENT DOCUMENTS

| | | | | |
|---|---|---|---|---|
| 3,953,611 A | | 4/1976 | Youngquist | 426/93 |
| 4,302,473 A | | 11/1981 | Mikami et al. | 426/46 |
| 4,368,151 A | * | 1/1983 | Howard et al. | 260/123.5 |
| 4,409,256 A | | 10/1983 | Johnson et al. | 426/656 |
| 4,771,126 A | | 9/1988 | Hirotsuka et al. | 530/378 |
| 5,270,200 A | | 12/1993 | Sun et al. | 435/240 |

FOREIGN PATENT DOCUMENTS

| | | |
|---|---|---|
| EP | 072617 A2 | 2/1983 |
| EP | 501117 A1 | 9/1992 |
| EP | 522800 A2 | 1/1993 |
| EP | 797928 A1 | 10/1997 |
| GB | 1 443 160 | 7/1976 |
| JP | 59109130 | 6/1984 |
| JP | 09075007 | 3/1997 |
| WO | WO 98 44807 | 10/1998 |

OTHER PUBLICATIONS

Sykes et al. Archived of Biochemistryand Biophysics 1981, vol. 210, pp. 525–530.*

Yakasaki et al. J. Argric. Food Chem. 1997, vol. 45, pp. 656–660.*

Nagano et al. J. Agric. Food Chem.. 1996, vol. 44, pp. 3484–3488.*

Nagano et al. J. Agric. Food Chem.. 1992, vol. 40, pp. 941–944.*

Dreau et al. J. Food Sci. Technol. 1994, vol. 31, pp. 489–493.*

Kitamura et al., Breeding trials for improving he food–processing quality of soybeans, Trends Food Sci. & Tech., 1993, pp. 64–67, vol. 4.

Nagano et al., Dynamic Viscoelastic Study on the Gelatin Properties of β–Conglycinin–Rich and Glycinin–Rich Soybean Protein isolates, J. Agric. Food Chem., 1996, pp./ 3484–3488, vol. 44.

Manzoni et al., Soybean Protein Products as Regulators of Liver Low–Density Lipoprotein Receptors. II. α–α' Rich Commercial Soy Concentrate and α' Deficient Mutant Differently Affect Low–Density Lipoprotein Receptor Activation, J. Agric. Food Chem., 1998, pp. 2481–2484, vol. 46.

Yagasaki et al., Biochemical Characterization of Soybean Protein Consisting of Different Subunits of Glycinin, J. Agric. Food Chem., 1997, pp. 656–660, vol. 45.

Yao et al., Effects of Maturation and Storage on Solubility Emulsion Stability and Gelatin Properties of Isolated Soy Proteins, JAOCS, 1990, pp. 974–979, vol. 67.

* cited by examiner

Primary Examiner—James Housel
Assistant Examiner—Baoqun Li
(74) Attorney, Agent, or Firm—Fulbright & Jaworski L.L.P.

(57) ABSTRACT

The utility of soybeans having a composition of greater than 40% of the protein as beta-conglycinin and less than 10% of the protein as glycinin for making highly functional high beta-conglycinin compositions was discovered. The discovered ingredients are useful for mimicking the texturizing properties of casein while also maintaining or improving physiological benefits of soy protein ingredients (e.g., cholesterol and triglyceride lowering properties). The high stability of the high beta-conglycinin compositions against protein—protein aggregation reactions is valuable for creating good tasting beverages and beverage mixes. Cheese with good spreadability, gloss and smoothness was made using an enzyme-modified version of the new ingredient composition. Cheese with good firmness and meltability was also created using a different enzyme-treatment. High beta-conglycinin compositions were found to demonstrate excellent emulsifying and gelling properties in the pH region (5.5–6.2) relevant to meat applications. High beta-conglycinin compositions also have possible use for improving the composition of essential amino acids for infant humans and animals.

13 Claims, No Drawings

HIGH BETA-CONGLYCININ PRODUCTS AND THEIR USE

CROSS REFERENCE

This application is a Divisional patent application of U.S. patent application Ser. No. 09/167,810, filed Oct. 7, 1998, now U.S. Pat. No. 6,171,640B, which is a Continuation-in-Part of PCT/US98/06579, filed Apr. 3, 1998, based on Provisional Patent Application Ser. No. 60/042,643, filed Apr. 4, 1997.

BACKGROUND OF THE INVENTION

The present invention relates to a high beta-conglycinin composition, meat analog, cheese analog, beverage and animal feed and to methods of producing a high beta-conglycinin composition, cheese analog, beverage, meat analog and animal feed.

The publications and other materials used herein to illuminate the background of the invention or provide additional details respecting the practice, are incorporated by reference.

Glycinin and beta-conglycinin (BC) account for approximately 70% of the proteins in soybeans. It has been postulated that the functional properties of soy protein ingredients in food systems can be improved by modifying the ratio of these proteins. Previous attempts have been to increase the ratio of glycinin to beta-conglycinin to improve the yield and quality of tofu-type soybean gels and to improve the content of sulfur amino acids for nutritional purposes (Kitamura, K., Trends Food Science & Technology 4:64–67, (1993), Murphy, P., et al., Food Technology 51:86–88, 110 (1997)).

Dietary proteins are needed to replace metabolic losses of tissue and organ proteins, to form and deposit protein in new tissues and to replenish tissue loss as a consequence of pathological conditions. These needs are met by indispensable (essential) amino acids and dispensable amino acids that comprise dietary proteins. It is largely in this context that the nutritional value of dietary proteins is defined as the ability to meet daily requirements for essential amino acids (Steinke, F. et al. New Protein Foods in Human Health: Nutrition Prevention and Therapy, CRC Press, 1992). High quality proteins contain all the essential amino acids at levels greater than reference levels and are highly digestible so that the amino acids are available. In this context, egg white and milk proteins are the standards to which other proteins are evaluated and plant proteins are considered to have inferior nutritional value. The essential amino acids whose concentrations in a protein are below the levels of a reference protein are termed limiting amino acids, e.g., the sum of cysteine and methionine are limiting in soybeans.

Glycinin contains 3 to 4 times more cysteine and methionine per unit protein than beta-conglycinin (Fukushima D., Food Rev. Int. 7:323–351, 1991). Thus it is expected that an increase in the content of glycinin and a decrease in the content of beta-conglycinin results in enhanced protein quality (Kitamura, K. Trends Food Science & Technology 4:64–67, 1993; Kitamura, K., JARQ 29:1–8, 1995). This is consistent with the finding that the mean value of the sulfur-containing amino acid contents in the seeds of four representative lines which were low in beta-conglycinin was about 20% higher than that of four ordinary varieties (Ogawa, T. Japan. J. Breed. 39:137–147, 1989). A positive correlation was also reported between the glycinin:beta-conglycinin ratio (1.7–4.9) and the methionine or cysteine concentration of total protein, among wild soybeans (Kwanyuen et al., JAOCS 74:983–987, 1997). There are no reports of the amino acid composition of high beta-conglycinin soybeans (glycinin:beta-conglycinin ratio less than 0.25).

In addition to the ability of proteins to meet the body's daily needs for essential amino acids, dietary proteins can also contribute bioactive peptides and amino acid patterns which can reduce the risk factors for cardiovascular diseases, cancer and osteoporosis. These compositional factors should also be considered in assessing protein quality, especially in countries such as the United States where people on the average consume a large excess of dietary protein. Researchers (Sugano, et al. PCT No. WO89/01495; Sugano, M. J. Nutr 120:977–985, 1990; Sugano. M. & Kobak, K. Annu. NY Acad. Sci. 676:215–222, 1993; Wang, M. J Nutr. Sci. Vitaminol. 41:187–195, 1995) have identified a pepsin-resistant fraction of soybean protein (5,000–10,000 molecular weight) that represents about 15% of the protein in isolated soy protein. Humans fed a diet with the pepsin-resistant fraction at 24 g or 48 g per day had lower LDL-Cholesterol and more fecal neutral and acidic steroid excretion than those fed diets with isolated soy protein or casein. The soy proteins which contribute to this pepsin-resistant fraction were not identified. Purified beta-conglycinin is more pepsin-resistant than purified glycinin (Astwood, J. & Fuchs, R. In Monographs in Allergy, Sixth International Symposium on Immunological and Clinical Problems of Food Allergy, Ortolani, C. and Wuthrich, B. editors, Basel, Karger, 1996), so it follows logically that beta-conglycinin may be a primary contributor to the bioactive fraction. This possibility has not been demonstrated yet in a feeding study, or with protein made from soybeans having altered protein compositions.

The alpha and alpha-prime subunits of beta-conglycinin specifically interacted with membrane components of human and animal liver cells in tissue culture experiments (Lovati, M. R., et al., J. Nutr. 126:2831–2842). The beta-conglycinin subunits were incorporated by the liver cells, degraded and caused an increase in the maximal binding of LDL to high-affinity receptors. It is proposed that such a mechanism could be responsible for the cholesterol lowering properties of soy protein isolates. However, it is not clear if significant amounts of dietary soy proteins can get to the liver in vivo. Lavarti et al. (J. Nutr. 122:1971–1978, 1992) reported a study in which hypercholesterolemic rats were fed either glycinin or beta-conglycinin for two weeks. Both groups showed a ⅓ reduction in total serum cholesterol. There are no studies which determine the effects of soy protein isolates from soybeans with modified soy protein compositions on the cholesterol lowering properties of soy protein isolate in animal models or humans.

It is reasoned from Rhesus monkey studies using alcohol extracted (which removes isoflavones) and non-alcohol extracted soy protein isolate, that soybean isoflavones are the primary components of soy protein isolates responsible for the cholesterol lowering effects (Anthony, M. S., J. Nutr. 126:43–50, 1996). However, subjecting soy protein to ethanol extraction did not have any effect on its lipid-lowering effects in other studies using hamsters (Balmir et al., J. Nutr. 126:3046–3053, 1996) or rats (Topping et al., Nutr. Res. 22:513–520, 1980). Alcohol extraction processes can extract some proteins and can denature and aggregate the unique structures of soy proteins, likely affecting how they act in the GI tract. For example, Sugano et al., (J. Nutr. 120:977–985, 1990) observed that methanol extraction completely eliminated the ability of high molecular weight soy protein peptides to bind and excrete steroids. Feeding isolated soy isoflavones (genistein and daidzein) had no Favorable effect on serum lipids or lipoproteins in humans (Colquhoun, et al., Atherosclerosis, 109:75, 1994; Nestel, P. J., Arterioscler. Thromb. Vasc. Biol. 17:3392–3398, 1997).

The confusion about the relative roles of various soy protein isolate constituents in the observed cholesterol-lowering effects, are difficult to resolve by using processing technologies to create samples with altered composition. An improved approach is to specifically modify the components of interest in the soybeans.

An emerging key indicator for the risk of heart disease, is high serum homocysteine levels. Dietary methionine is a precursor to homocysteine, so a high consumption of methionine can potentially increase consumers risk of heart disease, especially if they also consume low levels of folic acid and vitamin B6 (McCully, K. S., The Homocysteine Revolution, Keats Publishing, Inc., New Canaan, Conn., 1997). Another route which lowers the endothelial cytotoxicity of homocysteine is the reaction between nitric oxide (NO) and homocysteine in vivo to form the non-toxic S-nitroso-homocysteine. This route can be enhanced by increasing dietary arginine levels because arginine is converted by nitric oxide synthase to NO. Therefore, an ideal dietary protein for maintaining healthy levels of homocysteine, should have high arginine and low methionine (and cysteine), as is found in beta-conglycinin. However, the use of a beta-conglycinin rich soy protein isolate designed for this purpose has not been previously disclosed.

New protein ingredients must contribute positively to the taste, texture and appearance of foods to gain acceptance. These quality attributes are determined by the structure of the proteins and how they change in the presence of other food components (e.g., calcium ions, other proteins) and processing conditions (e.g., temperature, pH). Increasing the glycinin content of soybeans is usually proposed for improving food functionality of soy protein ingredients. Previous attempts to improve the yield and quality of tofu-type soybean gels have been to increase certain glycinins or the ratio of glycinin to beta-conglycinin (Wang, C -C. and Chang, S. J. Agric. Food Chem. 43:3029–3034, 1995; Yagasaki, K. et al. Breeding Sci. 46:11–15, 1996; Murphy, P., et al., Food Technology 51:86–88, 110, 1997). There is little information on the properties of glycinin and beta-conglycinin in other model food systems, especially under conditions typical of other food systems (e.g., low pH, high salt, fat, gel formation at temperatures below 72 degrees C.). Foaming properties of glycinin are superior to those of beta-conglycinin at a pH of 7.0 and no salt (Yu, M. A., J. Agric. Food chem. 39:1563–1567, 1991). Partially hydrolyzed glycinin forms heat-induced gels which are more similar to cheese curd than partially hydrolyzed beta-conglycinin at neutral pH (Kamata et al., Nippon Shokuhin kogyo Gakkaishi 36:557–562, 1989). Glycinin forms gels at boiling temperature with higher elastic moduli than soy protein isolate (Van Kleef, Biopolymers 25:31–59, 1986). Some comparisons were made between glycinin and beta-conglycinin at pH 7.5–8.0 (Shimada, K. and Matsushita, S., Agric. Biol. Chem. 44:637–641, 1980; Utsumi, S. and Kinsella, J. Food Sci. 50:1278–1282, 1985; Nakamura et al., Agric. Biol. Chem. 50:2429–2435, 1986). Though beta-conglycinin was observed to have superior emulsifying properties compared to glycinin, it did not have better emulsifying properties compared to whole soy protein isolate controls (Aoki et al., J. Food Sci. 45:534–546, 1980; Yao et al. JAOCS 67:974–979, 1990). The freeze-thaw properties of beta-conglycinin and glycinin rich soy protein isolates have not been reported, though the problem of soy protein freeze-thaw instability is known (Abtahi, S. and Aminlari, M., J. Agric. Food Chem. 45:4768–4772, 1997).

Soybean germplasm which lack glycinin, sib-line varieties B2W(2), B2G(2), and B2G(1) were received from Dr. Norihiko Kaizuma, President of Tohoku University, Morioka, Japan (1017/96). The mutation of these soybean lines was induced by using gama-irradiation (Odanaka, H. and N. Kaizuma, Japan J. Breed. 39 (Suppl.) 430–431, 1989; Kaizuma et al. Jpn J. breed. 40 (Supple 1) 504–505, 1990). These lines lack all of the group-I subunits consisting of $A_{1a}B_2$, $A_{1b}B_{1b}$ and $A_{2B}1_a$. Synthesis of the missing polypeptides has been shown to be controlled by a single recessive allele. No deleterious effects on physiological aspects such as seed development and germination were observed.

The properties of high beta-conglycinin isolates at pH 7 were discussed in Nagano, T. J. Agric. Food Chem. 44:3484–3488. The gel-forming properties at 85 degrees C. and foaming properties of enzymatically hydrolyzed beta-conglycinin fractions were discussed in Lehnhardt, W. F. and Orthoefer, F. T., European Patent No. 0072617, 1982. The concept of altering seed storage proteins by transgenic methods was made by Kinney, A., et al., International Publication No. WO 97/47731, however only attempts at eliminating beta-conglycinins were made and demonstrated.

Yields of protein and other soybean constituents also need to be considered in designing a commercially viable variety. Positive correlations were found between total protein content of soybeans and the glycinin:beta-conglycinin ratio, so the soybeans that were richer in glycinin had a higher protein content (Shui-Ho Cheng, 1984 Ph.D. thesis, Univ. of IL).

SUMMARY OF THE INVENTION

The present invention relates to a high beta conglycinin composition which has improved physical (e.g., stability and gelation) and physiological (e.g., cholesterol and triglyceride lowering) properties compared to commercial soy protein ingredients and methods of making the high beta-conglycinin composition. The present invention further relates to improved methods of food processing and the manufacturing food products. The present invention also includes methods for using the high beta-conglycinin composition as different food products.

In general, the present invention comprises a composition of greater than 40% of the protein as beta-conglycinin (BC) and less than 10% of the protein as glycinin (high BC composition). The high BC composition isolated by an acid precipitation process from high-BC soybeans grown in Illinois, had a sum of cysteine and methionine in the isolate greater than 25 mg/g protein, meeting the FAO.WHO requirements for 2–5 year olds. However, high beta-conglycinin made from high BC soybeans grown in Puerto Rico was high in arginine (75 mg/g protein) and low in methionine (less than 11 mg/g protein).

A method of manufacturing the high BC composition of the present invention comprises removing the hulls from soybean seeds and conditioning the seeds for flaking. The conditioned seeds are flaked and oil is extracted. The soybean seed flakes are then preferably ground and a solvent is added to bring the pH to a range from about 7.0 to about 10 to dissolve the protein. An extract is produced by removing the fiber by centrifuging and the extract is neutralized. Sugars and other low molecular weight solutes are removed by acidification near pH 4.6 or by ultrafiltration. The extract is either heat treated before removal (hb) of the low molecular weight solutes or after removal (ha), to make different types of high BC products. The resulting neutralized product is a slurry which is dried. It is further conceived that the beneficial properties resulting from the novel protein composition of high-BC soybeans are also useful in whole bean applications (e.g., snacks, cooked beans, tempeh) and in full-fat and defatted soybean flour and soy protein concentrate (e.g., texturized) made for bakery, dairy (after hydrolyzing the fibrous components using cellulases) and meat applications. The present invention also includes methods for using the high beta-conglycinin compositions as different food products.

DETAILED DESCRIPTION OF THE INVENTION

To provide an understanding of several of the terms used in the specification and claims, the following definitions are provided:

Beta-conglycinin: As used herein, the term beta-conglycinin refers to a trimer with a molecular weight mass of 150–200 kDa. Three major subunits of beta-conglycinin are the alpha-prime (72 kDa), alpha (68 kDa), and beta (52 kDa). The alpha-prime and alpha subunits contain two covalently bound carbohydrate moieties and the beta-subunit contains one. A review of the structure and properties of beta-conglycinin and the other major storage protein, glycinin is given by Utsumi et al., (in Food Proteins and Their Applications, Eds. Damodaran, S. and Paraf, A., Marcel Dekker, Inc., NY, 1997).

Group 1 glycinins: As used herein, the term group 1 glycinins refers to the subunits of glycinin classified as $A_{1a}B_1$, $A_2B_{1a}$, and $A_{1b}B_2$. The group 2 glycinins are $A_5A_4B_3$ and $A_3B_4$ (Nielsen, N. C., et al., Plant Cell 1:313, 1989). "A" refers to acidic subunits and "B" refers to basic subunit. The cysteine and methionine residue contents are higher in group 1 subunits than in group 2 subunits.

High beta-conglycinin soybeans: As used herein, high beta-conglycinin soybeans (high BC soybeans) refers to soybean seeds having greater than 40% of the protein as beta-conglycinin and less than 10% of the protein as glycinin using the analytical methods defined in Example 1.

Soy protein isolate (SPI): As used herein, soy protein isolate is a spray-dried powder made from soybeans containing not less than 90% protein (N×6.25) on a moisture-free basis.

Soy protein composition: As used herein, the term soy protein composition refer to food ingredients for humans or animals which contain soy proteins. Examples include soy flour, defatted soy flour, spray dried soymilk, tofu, spray dried tofu, soy protein concentrate, texturized soy protein concentrate and hydrolyzed soy protein and soy protein isolate.

High beta-conglycinin soy protein isolate: As used herein, high beta-conglycinin soy protein isolate (BC-SPI) refers to a spray-dried powder which is made from high BC soybean seeds. The amount of BC in BC-SPI is greater than 40% of the protein in the isolate and the amount of glycinin in BC-SPI is less than 10% of the protein in the solate using the methods in Example 1.

High beta-conglycinin composition: As used herein, the term high beta-conglycinin composition, or high BC composition, refers to food ingredients in which beta-conglycinin is greater than 40% of the soy protein and glycinin is less than 10% of the soy protein in the ingredient. Examples of food ingredients for humans or animals include soy flour, defatted soy flour, spray dried soymilk, tofu, spray dried tofu, soy protein concentrate, texturized soy protein concentrate and hydrolyzed soy protein and soy protein isolate.

Low beta-conglycinin soy protein isolate: As used herein, low beta-conglycinin soy protein isolate (low-BC-SPI) refers to a spray-dried powder which was made from soybeans lacking the alpha and alpha-prime subunits of beta-conglycinin. The beta-subunit of beta-conglycinin is present in the SPI (12% of the total protein).

BC-SPI-acid-hb: As used herein, BC-SPI-acid-hb refers to high beta-conglycinin SPI which is isolated by an acid precipitation process which received a heat-treatment before the acid precipitation step.

BC-SPI-acid-ha: As used herein, BC-SPI-acid-ha refers to high beta-conglycinin SPI which is isolated by an acid precipitation process which received a heat-treatment after the acid precipitation step.

BC-SPI-UF-hb: As used herein, BC-SPI-UF-hb refers to high beta-conglycinin SPI which is isolated by an ultrafiltration and diafiltration process which received a heat-treatment before the ultrafiltration process.

Cntrl-SPI: As used herein, control (cntrl) soy protein isolate refers to SPI which was made from a mixture of soybeans (Prospect, HP43 and Harovinton). Cntrl-SPI-acid-ha refers to SPI made from these soybeans which was isolated by an acid precipitation process which received a heat-treatment after the acid precipitation step. Cntrl-SPI-acid-hb refers to SPI made from these soybeans which was isolated by an acid precipitation process which received a heat-treatment before the acid precipitation step.

72C or 90C: As used herein, when the abbreviations above are followed by "72C," (e.g., BC-SPI-acid-hb, 72C) the heat-treatment during ingredient manufacture was at 72 degrees C. for 15 seconds. When the abbreviations above are followed by "90C" the heat-treatment during ingredient manufacture was at 90 degrees C. for 20 seconds.

L Value: As used herein, the term "L Value" is the measure of whiteness by a Hunter Lab calorimeter.

b Value: As used herein, the term "b Value" is the measure of yellowness by a Hunter Lab calorimeter.

Nitrogen Solubility Index (NSI): As used herein, the term "Nitrogen Solubility Index (NSI)" is the measure of protein solubility using Method Ba11-65 of the Official and tentative Methods of the AOCS, 1989, 4th Edition.

Partially Hydrolyzed: As used herein, the term "Partially Hydrolyzed" means that the soy proteins were cleaved into smaller polypeptides, but not predominately to amino acids or peptides less than 1,000 molecular weight.

Emulsified Meats: As used herein, the term "Emulsified Meats" means products where fat is dispersed into droplets and stabilized by a protein network having a tender texture, such as frankfurters (hot dogs) and bologna.

Nutritional Food Bar: As used herein, the term "Nutritional Food Bar" means a food bar designed to promote health.

Mouthfeel: As used herein, the term "Mouthfeel" means how the substance feels in a human mouth.

Com'l SPI: As used herein, commercial SPI (Com'l SPI) refers to SPIs which can be purchased from manufacturers of SPIs. As used herein, Com'l SPI A, B, C, D and G are Supro 760, Supro 974, Supro 670, Supro 500E and Supro 710, respectively, are from Protein Technologies International, St. Louis, Mo. These isolates are produced for different applications. Supro 760 is recommended by the manufacturer specification sheets for pasteurized, retort or UHT processed beverages and frozen desserts, dips and yogurt. Supro 940 is recommended for emusifying and aerating properties as an egg protein substitute. Supro 670 is a partially hydrolyzed soy protein isolate recommended for use in dry beverage mixes, imitation cheese and food bars.

Supro 500E is recommended for meat applications and Supro 710 is a hydrolyzed soy protein isolate recommended for liquid coffee whiteners requiring freeze/thaw stability, frozen desserts, dips, yogurts and imitation cheese. As Used herein, Com'l SPI E and F are ProFam 974 and Ardex DHV, respectively, from Archer Daniel Midland, Decatur, Ill. ProFam 974 is recommended for milk replacers, processed meats, emulsified meats and sausage-type meats.

BBI: As used herein, the term Bowman Birk Protease Inhibitor (BBI) refers to a family of related proteins found in many plant seeds having a molecular weight of from 7,000 to 8,000 which inhibit both trypsin and chymotrypsin. The small inhibitor (70–80 amino acids with 7 disulfide bonds) is highly heat stable; for example, no large conformation change was induced by heating at 80 degrees C. for 1 hour at pH 6.5 (Wu, Y. V. and Sessa, D. J. J. Agric. Food Chem. 42:2136–2138, 1994).

KTI: As used herein, the term Kuintz Trypsin Inhibitor (KTI) refers to a protein which consists of a single polypeptide chain of 181 amino acids, and has a molecular weight of 21,500. It contains two methionine and four half cystine residues (Laskowski and Kato, Annual Review of Biochemistry 49:593–626, 1980)

The present invention reveals physiological as well as food functionality benefits of the high BC composition. The high BC composition of the present invention has higher than expected levels of essential amino acids. The high BC composition of the present invention has improved properties for food processing and products.

Assessing the Value of Proteins in Fat-Containing Foods

Fat-containing food products such as frankfurters, processed cheese, salad dressings, sauces, and nutritional beverages depend on emulsifiers to help form very small fat droplets during homogenization processes and then stabilize the droplets against coalescence (fusing of droplets) and creaming (floating to the top) during storage. Proteins which are especially good emulsifiers have highly flexible structures which allow high affinity and adsorption of the proteins at the oil-water interfaces, followed by the ability to form mechanically strong and viscoelastic and highly hydrated films on the droplet surfaces via protein—protein interactions. In some products controlled aggregation of the protein-stabilized fat droplets following heating or enzymatic hydrolysis of proteins, is important for forming gel structures which hold water and provide texture to foods. Animal proteins such as caseins in milk, lipoproteins in egg yolk, myosins in meat and albumin proteins in egg white are good emulsifying agents which have both stabilizing and gel-forming properties (Bringe, N., In "Food Proteins and Lipids," Damodaran, S., ed., Plenum Press, NY, pp. 161–181, 1997). The opportunity of the instant invention is to replace animal proteins with less expensive and healthful soy protein ingredients.

The potential of new protein sources to replace animal proteins as food emulsifiers can be determined by measuring the diameter of protein-stabilized fat-droplets which are formed under conditions which break the fat particles into small droplets. A good protein emulsifier adsorbs to the new oil-water surfaces quickly and stabilizes the droplets from coalescence, resulting in emulsions having the smallest median particle diameters. Poor emulsifying proteins do not cover ail of the new oil-water surfaces and have poorly hydrated structures which do not repulse (prevent aggregation with) other protein-covered droplets. The poor protein emulsifiers cause the formation of larger particles via droplet—droplet aggregation and the large particles rise in space with time leaving a serum layer at the bottom of suspensions. Large particle aggregates are also detected in the mouth as chalky or gritty textures. Small particles are not detected in the mouth as individual particles and create a smooth or creamy texture (Bringe, N. and Clark, D. In "Science for the Food Industry of the 21st Century", Yalpani, M. ed., ATL Press, pp. 51–68, 1993). Measurements of the median diameter of protein-covered oil droplets are a sensitive measure of the stability of the proteins to protein—protein aggregation under various conditions and are also relevant to the stability or aggregation properties of the proteins in the absence of fat. To determine the potential of new protein ingredients to replace other ingredients, one can prepare emulsions with the ingredients under various conditions relevant to different foods and determine the sizes of the droplets formed and the amount of serum created after storage (Bringe, N. et al., J. Food Sci. 61:1–6, 1996). The relative differences in the median particle diameters of protein stabilized emulsions used in this study did not change significantly over 10 days of storage.

Beneficial Functional Properties of Purified Beta-Conglycinin (BC)

Before high BC soybeans were available for testing, the properties of purified BC were compared to glycinin and commercial isolates in model food emulsions. In the instant invention we discovered that BC formed smaller emulsion particles than control and commercial soy protein ingredients when the emulsions were prepared in the presence of ionic sodium (or potassium) or ionic calcium at levels similar to that found in foods such as nutritional beverages. (See Example 2) The good emulsifying properties of BC are important for keeping beverage emulsions from separating (creaming).

Further aspects of the invention include the discoveries that BC performed better than control and commercial soy protein ingredients when the protein-stabilized emulsions were heat-treated or when the emulsions were frozen and thawed as described in Example 2. This property is valuable in applications such as frozen desserts and liquid frozen coffee whitener where the smooth homogenous textures and appearances of the products depends on the stability of the proteins against freeze-thaw-induced protein aggregation.

Another embodiment of the invention is that heat-induced gel or viscosity forming properties of BC stabilized emulsions were optimum near pH 5.6 and significantly greater than control and other soy protein ingredients in the presence of salt as described in Example 2, Table 3. The preparation of food gels from BC-stabilized emulsions in the pH range 5.4 to 5.8 and low salt concentrations (0.2–0.6% NaCl or KCl) can now be conceived and designed under this invention. The gelling property is in the pH region of emulsified meats where soy protein ingredients are used as gelling agents. Vegetarian meat-analog products are not restricted to high salt formulations and are relevant to the discovered gelling properties of beta-conglycinin under low salt conditions.

Soy Protein Composition

The present invention relates to high beta-conglycinin composition, meat analog, cheese analog, beverage and animal feed. The choice of particular soy protein composition is, in part, determined by the intended end use and whether the other components of the soybean are desired (e.g., fiber, isoflavones, oligosaccharides, pigments, enzymes). For example, the common use of soy protein flour is in bakery products, spray dried soymilk and spray dried tofu in organic food bars and cheeses, texturized soy protein concentrates in meat products, and soy protein isolates in beverage and cheese products. The state of the protein in the composition is also altered for various applications. For example, denatured soy protein is desired for making some emulsified meats, highly soluble protein is desired for beverages and partially hydrolyzed protein is desired for cheese. Suitable procedures, material and methods related to protein composition preparation and use in food applications may be found in Liu, KeShun, Soybeans-Chemistry, Technology and Utilization, Chapman & Hall, NY, (1997); Erickson, D. R., editor, Practical Handbook of Soybean Processing and Utlization, AOCS Press, Champaign, Ill. and United Soybean Board, St. Louis, Mo., (1995); Applewhite, T. H. (ed.) Proceedings of the World Congress on Vegetable Proteini Utilization in Human Foods and Animal Feedstuffs, American Oil Chemists' Society, Champaign, Ill. (1989); Soy Protein Products—Characteristics, Nutritional Aspects and Utilization, Soy Protein Council, Washington D.C. (1987); Hua, Y. F., et al., J.A.O.C.S. 73:1067–1070 (1996); described herein.

The following disclosed methods refer to the use of soy protein isolates, however, those skilled in the art would know how to utilize other types of soy protein composition (as defined in the Definitions) in production of the food products described herein.

BC-SPI

To take advantage of the properties of BC in the above applications, an economical means of preparing compositions which are rich in BC and lacking in glycinin was developed in the present invention. The use of high BC soybeans which contain less than 10% glycinin and more than 40% BC (Example 4, Table 7), enable the preparation of BC-SPI without the inefficiencies of removing glycinins during processing. The BC-SPIs of the present invention contained 50–62% BC, compared to 26–29% in commercial SPI (Example 4, Table 6). Also the BC-SPI of the present invention contained approximately 3–6% glycinin compared to 40–45% in commercial SPI (Example 4, Table 6).

High BC soybeans seeds were processed into BC-SPI by using acid precipitation and a combination of ultrafiltration and diafiltration methods (Lawhon, J., U.S. Pat. No. 4,420, 425, 1983; Koseoglu, S. and Lusas, E., In "Proceedings of the World Congress on Vegetable Protein Utilization in Human Foods and Animal Feedstuffs, ed. Applewhite, T., Amer. Oil Chem. Soc., Champaign, Ill., pp. 528–547, 1989) as described in Example 3. Low-BC seeds (no alpha or alpha-prime subunits; beta-subunit of BC was 12% of total protein) were also processed into soy protein isolate for comparison in hamster feeding studies.

Solubility and Color of BC-SPI

Proteins are soluble in water when the electrostatic and or hydration replusion between proteins is greater than the driving force for hydrophobic interactions (Kinsella et al. In Developments in Dairy Chemistry—4, Fox, P. F. (Ed), Elsevier Applied Science, London, pp. 55–95, 1989). Protein molecules aggregate to form colloidal and macrocolloidal particles when too many hydrophobic groups are exposed to water, causing water to become more structured (hydrogen bonded) around those groups and lose entropy. The primary driving force for the aggregation of protein monomers is the increase in entropy of water, which occurs as predominatly hydrophobic regions of the protein surfaces associate and ionic groups pair within those interaction sites (Bringe, N. A. & Kinsella, J. E., in Developments in Food Proteins, Vol. 5, Hudson, B. J. F. (Ed.), Elsevier Applied Science Publishers LTD, Barking, England, pp. 159–194, 1987). When globular proteins such as soy proteins are heated (70–95 degress C.), the proteins increasingly unfold, exposing more hydrophobic amino acids. This denaturing results in greater amounts of aggregation (Hayakawa, S. & Nakai, S. J. Food Sci. 50:486–491, 1985). Proteins can also be denatured by other treatments such as high pressure and alcohol. The extent of denaturation and aggregation for a given treatment depend on conditions (e.g. pH) which affect the structure (e.g., net negative charge and hydration) of the proteins. Measures of particle size and soluble protein serve as a measures of protein denaturation. However, the solubility of denatured and aggregated proteins varies. For example, one can partially resolubilize denatured and aggregated proteins created during soy protein concentrate manufacture by using heat and mechanical action to transform the strongly bound protein molecules to loosely interacting aggregates (Hua, Y. F. et al. JAOCS 73:1067–1070).

Highly soluble and white protein compositions are valuable for dry beverage mix applications where low shear mixing is used to disperse the powder (rather than industrial homogenizers) and where the white color of dairy beverages is desired.

In one embodiment of the invention, the solubility, particle size distributions and color of the BC-SPI-UF-hb and BC-SPI-acid-ha were substantially better than BC-SPI-acid-hb and commercial isolates (Example 4). Only the BC-SPI-UF-hb had a whiteness (L) value greater than 86.5 and a yellowness (b) value less than 10. Only BC-SPI-acid-ha had less than 10% of the particle volume greater than 10 microns after dispersion in water for 10 minutes.

The low portions of large aggregates (>10 microns) in the BC-SPIs reduces objectionable gritty mouthfeel in food applications. The high solubility of the BC-SPIs also relates to good functional properties discussed below (e.g., emulsifying properties, stability against protein—protein aggregation reactions during freezing and thawing).

Stability of BC-SPI Near pH 6.7, Beverage Model

Sodium caseinate is valued in beverages for its ability to form and stabilize small fat droplets and for its resistance to protein—protein aggregation reactions in the presence of calcium, low pH (e.g., 5.5–6.5), freezing and high temperatures (>75C). The presence of kappa-casein in casein ingredients which has a hydrated and negatively charged region in its structure, is largely responsible for the stability of the caseins (Bringe, N. A. and Kinsella, J. E. 1991. J. Dairy Res. 58:195–209). It is also possible that a few of the soy proteins are largely responsible for the emulsifying and stability properties of soy protein ingredients. The net negative charge of beta-conglycinin is much lower than that of glycinin as measured by the apparent isoelectric pH of the two protein complexes (4.8 and 6.4, respectively) (Thanh, V. H. and Shibasaki, K. J. Agric. Food Chem. 24:1117, 1976; Brooks, J. R. and Morr, C. V. JAOCS 62:1347, 1985). Therefore beta-conglycinins have the potential to mimic the properties of sodium caseinate, especially the alpha-subunits of beta-conglycinin which have the lowest isoelectric pH of the beta-conglycinins and highly hydrated N-terminal regions (Morita, S., et al., Biosci. Biotech. Biochem. 60:1870–1871, 1996).

The properties of the BC-SPIs were compared to commercial soy protein isolates and sodium caseinate in a model beverage system to determine if an increase in the composition of beta-conglycinin in a pasteurized and spray-dried soy protein ingredient was beneficial. The BC-SPI's performed as well or much better than control and commercial SPI's depending on the BC-SPI and conditions (Example 6). It was discovered that BC-SPI-acid-ha had much greater stability against calcium ion induced aggregation, pH (6.5) induced aggregation, and heat-induced aggregation than controls and commercial SPI's (Example 6). The stability of BC-SPI-acid-ha against aggregation as measured by emulsion particle diameter, was similar to the stability demonstrated by purified BC (Example 2). The stability of BC-SPI-acid-ha proteins mimic those of sodium caseinate and are useful for beverage applications such as nutritional beverages, infant formula and soymilk. Therefore an aspect of this invention is the development of beverages and the use of BC-SPI to obtain good texture.

This invention also includes the discovery that the BC-SPI of the present invention have a high degree of freeze-thaw stability which was better than that of whole and partially-hydrolyzed commercial SPI as discussed in Example 6. The Cntrl-SPI-acid-ha ingredients also had good freeze-thaw stability. Therefore an aspect of the invention is the process used to make the highly soluble BC-SPI and Cntrl-SPI compositions as described in example 3C.

The freeze-thaw stability of BC-SPI-acid-hb was lost when free calcium ions (4 mM) were included in the formation (median particle diameter>100 icrons). Emulsions prepared using BC-SPI-acid-ha and Cntrl-SPI-acid-ha showed better stability (median diameter of emulsions were 10 microns after freeze-thaw treatment in the presence of calcium, 4 mM and NaCl, 70 mM). Therefore an aspect of the invention is the use of highly soluble BC compositions such as BC-SPI-acid-ha to achieve good freeze-thaw stability.

Thickening Properties of BC-SPI at pH 5.8, an Emulsified Meat Model

Commercial soy protein isolates are typically heat-treated at 90–154 degrees C. for up to 20 seconds during manufacture to sterilize the isolate and denature the proteins. The heat-treatment can facilitate the gelation of the soy protein isolates in food products where the maximum food processing temperatures are below the denaturation temperatures of native soy proteins. To test the application of BC-SPI for gelling properties at the pH, salt and temperature conditions of emulsified meats, we compared the gelling properties of BC-SPI with and without highly denaturing the proteins (at 90 degrees C.), to the gelling properties of commercial isolate and egg white. Egg white is an excellent gelling agent used in numerous foods including meat products such as surimi (crab leg analogs). However, like meat protein, egg white is expensive compared to soy protein. One unexpected finding of the present invention was that the viscosities of the emulsions prepared with BC-SPIs were 1.7–3.0 times greater than those prepared with the commercial SPI's and were closest to performing like egg white (Example 7, Table 14). Furthermore the water-holding structures formed by protein—protein interactions between the surfaces of protein-coated fat droplets were more easily broken down in the emulsions stabilized by BC-SPI than in those stabilized by commercial isolate, as measured by the greater decreases in viscosity with increase in shear time (Example 7, Table 14). When this breakdown occurs in the mouth it is perceived as a more desirable texture, e.g., smoother, juicy and less tough. Therefore, the gelling (and related fat and water binding) properties of soy protein isolate under the conditions of emulsified meat systems can be optimized by using BC-SPI.

An explanation for the positive effects of denaturing high BC compositions to form gels is as follows: Highly-denatured high BC compositions were made at dilute concentrations at approximately pH 7.0 and 90 degrees C. where protein denaturation occurs to expose reactive sites, but aggregation of the denatured proteins is limited. The highest viscosities (or firmness, or related water and fat binding) occur when denatured protein is exposed to conditions which are optimum for the formation of fine gel/aggregate structures. This gelling condition is near pH 5.6–6.0 for BC and gelation of denatured BC occurs faster and at lower temperatures (at or below the denaturation temperature of native BC) when BC is predenatured. BC-SPIs were tested for comparison with highly denatured BC-SPIs. The difference between the viscosities of the samples made with un-treated BC-SPIs and those made with highly denatured BC-SPI quantify the value added by pre-denaturing the soy proteins using a high heat treatment. There is less value added by highly denaturing normal SPI because glycinin forms complexes with BC changing the nature and quantity of subsequent gel-forming reactions (e.g., optimum gelling conditions are moved to different pH values and there are fewer non-aggregated sites on BC available for gel formation).

The good emulsifying and gelling properties of denatured high BC compositions require a significant amount of shear to dissociate and hydrate the protein aggregates. Some meat or meat-analog processes involve much less shear. This invention includes the discovery that under low shear conditions (20 seconds sonication rather than 60 seconds), highly soluble BC-SPI-acid-ha stabilized smaller fat droplets and, after heat-treatment of the emulsion, formed greater viscosities than commercial soy protein isolates (Example 7, Table 15). Therefore the emulsifying and binding properties of SPI can be optimized in products such as batter coated meat pieces by using the more highly soluble (less denatured) BC-SPI-acid-ha. The emulsions created using Cntrl-SPI-acid-ha ingredients also formed much higher viscosities following heat-treatment than commercial ingredients indicating that the process used to make the highly soluble BC-SPI and Cntrl-SPI compositions as described in example 3C is an aspect of the invention.

Thickening or Gel-Forming Properties of BC-SPI-acid-ha at 0.5% NaCl in Water Phase, a Model for Vegetarian Meat and Other Acid Gels BC-SPI-acid-ha of this invention was found to have much greater gel-forming properties than commercial isolates and a control SPI, near pH 5.6 and low NaCl (0.5% in water phase). These findings for BC-SPI-acid-ha suspensions heated to 70 degrees C. or 80 degrees C. (Example 7) replicate the discovery of the good thickening properties of pure beta-conglycinin heated at 90 degrees C. (Example 2, Table 3). The use of the gelling or thickening property of highly soluble high-BC compositions such as BC-SPI-acid-ha is therefore conceived for making vegetarian meat analogs (e.g., hot dogs) and other acid gels (e.g., yogurt-analogs, bakery fillings) in the pH range 5.2–5.6.

Amino Acid Composition of BC Soybeans and BC-SPI

High BC soybeans of this invention were surprisingly high in protein and in the contents of methionine, cysteine, lysine and arginine amino acids. (See Example 7) These amino acids are normally limiting in soybeans and soybean meal, especially for infant animals and humans (DeLumer, B. et al., Food Technol. 51:67–70, 1997). Therefore one aspect of the present invention includes the use of high BC soybeans to make soybean meal (full fat and defatted) which is rich in essential amino acids for use in animal feed, limiting the amount of synthetic amino acids that are needed to fortify feed rations. to realize the benefits of these amino acid levels, it is conceived that further seed modifications or blending with tryptophan rich proteins sources are needed to prevent tryptophan concentrations from being limiting.

The high BC soy protein compositions made by the processes described in Example 3, were either similar in essential amino acid composition to that of commercial soy protein isolates or rich in sulfur amino acids as shown. (See Example 10) So the uses of the high BC compositions for various food texture and physiological benefits are not necessarily limited by an imbalance of essential amino acids. The likely explanation is that the high BC soybeans were also enriched in minor soy proteins as part of the compensation for the loss of glycinin and these proteins are retained in the high BC compositions.

Cholesterol and Triglyceride Lowering Properties of BC-SPI

Soy protein isolates were made from either soybeans which included or which did not include the alpha and alpha-prime subunits of BC. These BC-SPIs and control isolates made form normal soybeans were tested for cholesterol and triglyceride lowering properties using hamsters and published methods (Terpastra, A. et al., J. Nutr. 121:944–947, 1991; Potter, S., et al., J. Nutr. 126:2007–2011, 1996; Balmir, F. et al., J. Nutr. 126:3046–3053, 1996).

Hamsters consuming the BC-SPI based diet for 6 weeks had significantly lower total cholesterol and triglyceride concentrations than those fed Cntrl-SPI, Com'l-SPI A or sodium caseinate (Example 5; $P<0.05$). The reductions in serum cholesterol and triglycerides on the BC-SPI diet, compared to the sodium caseinate group, were 28% and 73%, respectively. The reduction in cholesterol was largely due to a significant reduction in the LDL and VLDL cholesterol fraction ($P<0.05$). The hamsters consuming the BC-SPI base diet also had a lower total serum cholesterol and triglyceride concentrations than those fed the low-BC-SPI diet. The differences in total cholesterol concentrations between the BC-SPI and low-BC-SPI groups was not significantly different ($P=0.057$). The differences in triglyceride concentrations between the two groups was significantly different ($P<0.05$). The food intake was reduced in the BC-SPI group by an average of 16% compared to the other soy isolate-containing diets and casein diets ($P<0.02$). There was no difference in food intake between the other diets.

The results of this study provide new information about the active components in SPI which are responsible for the cholesterol and triglyceride lowering properties. The alpha and alpha-prime subunits of BC and higher levels of isoflavones were not required. The absence of the alpha and alpha-prime subunits of BC in the low-BC-SPI did not cause this isolate to have poor cholesterol or triglyceride lowering properties. The low-BC-SPI had 2.4–2.8 times less isoflavones than the Com'l-SPI A or Cntrl-SPI, but caused the same or greater reductions in cholesterol and triglycerides. The A3 subunit of glycinin reportedly gives rise to a bile acid binding protein following pepsin-pancreatic digestion (Iwami et al., Tanpakushitsu Kenkyukai kaishi 15:74–80, 1994). However, the lower amount of A3 protein in BC-SPI (Example 4, Table 6) did not limit the cholesterol and triglyceride lowering properties of the SPI.

Components related to the trypsin inhibitor activity of the SPIs may be important in determining the cholesterol and triglyceride lowering properties of the SPIs. Supporting this are the linear regressions between the total cholesterol and triglyceride contents of the hamsters on the SPI diets (Example 5, Table 10) and the trypsin inhibitor activity of the SPIs (Example 4, Table 6) which had R-squared values of 0.98 and 0.88, respectively. One possible explanation for the results is that the lower food intake alone accounted for the significantly lower lipid levels observed in the BC-SPI group compared to the other SPI groups, by reducing the amount of dietary fat and cholesterol consumed by the hamsters. The mechanism for the reduced food intake of the BC-SPI may be that poorly digested protein resulting from the high trypsin inhibitor activity delayed nutrient absorption and result in decreased food intake (Schneeman, B. O., Am. J. Clin. Nutr. 42: (Suppl. 5: 966–972, 1985). Alternatively, it may be that trypsin inhibitor caused an increased secretion of the satiety factor, cholecystokinin (CCK), through the direct inhibition of trypsin as found in Zucker rats (McLaughlin C L et al., Physiol. Behav. 31:487–491 1983). In addition SPI's with higher trypsin inhibitor activity may be digested to a lower extent by trypsin, resulting in a greater concentration of soy protein fragments which can physically interact with bile acids and cholesterol in the intestine. The interaction with bile acids reduces absorption of bile acids and associated cholesterol and increased excretion of cholesterol, cholesterol metabolites, neutral steroids and bile acids in feces. Such an increase in cholesterol excretion likely upregulates LDL apo B/E receptor activity in the liver to remove cholesterol from the blood and increase the supply of cholesterol into the bile acid synthesis pathway (Beynen, A. C., J. Nutr. Sci. Vitaminol 36(Suppl):S387–S93, 1990). However, total neutral sterol excretion (cholesterol and coprostanol, the major intestinal cholesterol metabolite) for all the experimental groups consuming the the soy isolate-containing diets were similar to each other and 25% higher than neutral sterol excretion in the casein group (Example 5, Table 10). Similarly, fecal excretion of bile acids for hamsters on all the soy isolate-containing diets was 5-fold greater than that of the casein diet but there was no difference in the fecal bile acid excretion between the different soy isolate-containing diets. In addition, hepatic cholesterol concentrations were reduced by 39% on average in hamsters fed the soy isolate-containing diets compared to casein and there were no significant differences in hepatic cholesterol reductions between the soy groups. Neither fecal bile acid excretion nor hepatic cholesterol concentrations in hamsters fed the soy isolate-containing diets correlated with serum cholesterol levels.

Despite the similarities in the apparent mechanism of lipid lowering between the different soy protein isolates, BC-SPI had significantly better cholesterol and triglyceride lowering properties than Com'l SPI A. The more effective serum cholesterol lowering by BC-SPI versus Com'l SPI A is not explained by an increase in fecal bile acids or total neutral steroid excretion since BC-SPI and Com'l SPI A had similar increases (not significant) in these parameters (versus casein). The fecal concentration of cholesterol was increased by 54% ($p<0.05$) in the BC-SPI group compared to the Com'l SPI A group, while coprostanol was decreased by 20%, suggesting a reduced breakdown of cholesterol in the BC-SPI group. It is not clear whether this alteration in fecal cholesterol metabolism by BC-SPI alone can fully account for the differences seen in the degree of serum cholesterol lowering between BC-SPI and Com'l SPI A experimental groups (reductions of 28% and 15%, respectively compared to casein group). Therefore there are other unique properties of the BC-SPI which may account for the more efficacious cholesterol and triglyceride lowering properties.

BC-SPI had higher trypsin inhibitor activity because the high BC soybeans were rich in Bowman Birk Inhibitor (BBI) and higher levels of this protease-inhibitor were retained in the BC-SPI (Example 4, Table 6 & 7). There was a relationship between the amount of BBI in the SPIs and the serum lipid contents, so it is also possible that BBI content, rather than general trypsin inhibitor activity, was a key factor affecting serum lipid levels. BBI is an alcohol soluble protein and its extraction from soy can partly explain why others found alcohol-extracted soy protein less able to mediate an effect on lipid parameters (Kirk, et al., J. Nutr. 128:954–959, 1998; Anthony, M. S. et al., J. Nutr. 126:43–50, 1996). Another explanation by Sugano et al. (J. Nutr. 120:977–985, 1990) is that alcohol extraction changes the structure of the soy proteins such that the undigested fragments no long bind to bile acids and cause excretion of cholesterol. An aspect of this invention is the use of high BC soybeans and protein ingredients derived from high BC soybeans and the use of BBI in combination with soy storage proteins as nutritional supplements for maintaining healthy (low) cholesterol and triglyceride levels.

In applications such as infant formula where protease inhibition is undesirable, it is conceived in this invention that one can use soy processing technologies or genetic engineering techniques to remove the inhibitors and or inhibitor activities.

BC-SPI as a Source of Anticancer BBI, Antioxidant Peptides, and Immunity Activating Peptides Bowman Birk Inhibitor (BBI) prevents or reduces various types of induced malignant transformation of cells in culture and of tumors in experimental models in animals (Kennedy, A. J. Nutr. 125: 733S–743S, 1995). Therefore there is an interest in identifying soy-based foods which people have been consuming which contain significant levels of active BBI (Miyagi, Y. J. Nutr. Sci. Vitaminol. 43:575–580, 1997; Billings, P. C. et al. Nutr. Cancer 14:85–93, 1990). The high content of BBI in high BC compositions of this invention now offer an economical source of BBI-rich material for improving the composition of BBI in soy-based foods and reducing the need to consume BBI as isolated component in a supplement or a drug. High BC compositions such as BC-SPIs (Example 4) which are made from high BC soybeans, are conceived in this invention for increasing dietary consumption of BBI for maintaining healthy (non-cancerous) tissues. An aspect of this invention is that the BBI content of the isolate can be enriched by using ultrafiltration and diafiltration to make SPI (Example 4, Table 6). This contrasts to the control made by ultrafiltration at pH9, where BBI was not retained in the SPI (Example 4, Table 6). the content of BBI in cultured soybean cotyledons has also been increased by methionine and sulfate supplementation (Biermann, B. J., et al., J. Agric. Food Chem. 46:2858–2862, 1998). Other technologies target the reduction of BBI in soybeans (Beach, L., et al., International patent number WO 95/27068, 1995).

Research studies which evaluate the healthful properties of peptides found in soy protein digests have revealed that beta-conglycinin is a source of antioxidant (Chen et al. J. Agric. Food Chem. 44:2619–2623, 1996) and immunity activating peptides (Tanaka, M. et al. Nogei Kagaku Zasshi 68:341, 1994). It was discovered that the antioxidant (LLPH) and the immunity activating (MITLAIPVNKPGR) peptides are only found in beta-conglycinins. Therefore it is conceived that high BC composition of this invention offers a rich dietary source of these beneficial peptides for maintaining health.

BC-SPI for Processed Cheese Applications

In processed cheese applications of the present invention, protease-treated BC-SPIs were used to create elastic type processed cheese which fractures or a spreadable cheese. There are several differences between the structure of casein proteins and soy proteins. One key difference is that the primary caseins (alpha-s1- and beta-caseins) lack cysteine, whereas the five soy glycinin subunits each contain 6–8 cysteines and the beta-conglycinin subunits contain 0 or 1 cysteine (Utsumi et al. In Food Proteins and Their Applications, Eds. Damodaran, S. and Paraf, A., Marcel Dekker, Inc., 1997). Beta-conglycinin is more similar to caseins in this respect than glycinin, so fewer defects caused by sulfur groups are likely in the cheese lacking glycinin (e.g. sulfur-based flavors, disulfide-linked protein aggregates which hold water and create mealy texture).

Another key difference between casein proteins and soy proteins is that the caseins are phosphorylated. The phosphate groups of casein proteins serve two roles. The first role in natural cheese is to make the casein proteins insoluble in the presence of calcium following the addition of the enzyme chymosin which specifically cleaves kappa-casein. The second role is to resolubilize or hydrate the caseins following acidification by bacterial cultures, and removal of water (whey). At the lower pH, calcium is released from the phosphoproteins and the hydrated phosphate groups limit protein—protein interactions. In processed cheese, the pH does not have to be lowered as far to solubilize the caseins, because various phosphate salts are added which chelate calcium ions. The limited nature of the casein—casein interactions at pH of 5.1–6.0 and at high food preparation temperatures, reduces the water-binding and hence viscosity of the protein-stabilized oil-in-water emulsion, and enables the caseins to flow as demonstrated by the melting and stretching properties of the cheese. The solubilized caseins also serve a critical role as emulsifying agents in processed cheese, which prevent the separation of fat during cooking.

Beta-conglycinin is a glycoprotein which contains covalently attached carbohydrates. These carbohydrates which remain hydrated at the pH of cheese, limit protein—protein interactions between BC proteins. The solubility of BC proteins at the pH of cheese can be further improved by partially hydrolyzing BC using an enzyme such as Alacalase (Novo Nordisk), and this change in protein structure and properties resulted improved melting properties of processed cheese analog made with BC-SPI (30% of the cheese protein) (Example 11). The melting properties of processed cheese analog containing normal SPI are also improved by partially hydrolysis (Kim, S. et al. JAOCS 69:755–759). The removal of additional cysteine-rich proteins from high beta-conglycinin compositions should also improve the properties of hydrolyzed BC in processed cheese.

BC-SPI was also hydrolyzed using an enzme called Flavourzyme (Novo Nordisk). The use of this product (30% of the cheese protein) in combination with rennet casein created a most dramatic change in the processed cheese analog texture (Example 11). This cheese was glossy in appearance, very spreadable and smooth in texture, similar to a cheese spread or cream cheese. The cheese had only a mild soybean flavor. The good taste of the cheese is a result in part of the low amounts of aldehydes present in the high BC compositions used to make the cheese. The composition of thiobarbituric acid reactive substances in BC-SPI-acid-ha 72C and BC-SPI-acid-ha 90C were 0.522 and 0.688 mg malondialdehyde/kg., respectively. These are similar or lower values than that of commercial SPIs we tested (e.g., Com'l SPI E had TBA value of 0.771 mg/g). The TBA tests were done at Ralston Analytical Laboratories, St. Louis, Mo. following Yu, T. C. and Sinnhuber, R. O., J.A.O.A.C. 44:256–258, 1967. An aspect of this invention is the discovery that the use of enzyme-treated BC-SPI can be used to create a spreadable cheese product with good taste containing at least 30% of the protein as soy protein and less than 48% moisture.

In the instant invention it is further conceived that the partial hydrolysis of BC is valuable for creating unique soy-based food textures because it is possible to specifically cleave BC proteins in half to form 30 kDa fragments (Kawai et al., Biosci. Biotech. Biochem. 61:794–799, 1997).

Low Methionine, High Arginine Protein for Homocysteine

Methionine derived from dietary proteins serve as one of the major sources for the biosynthesis of sulfur amino acids including homocysteine. Homocysteine is a key risk factor of cardiovascular disease. Prolonged consumption of low methionine diet will, therefore, reduce or at least maintain the plasma level of homocysteine.

Arginine, on the other hand, is the natural substrate for nitric oxide synthase, which converts arginine to citrullin and nitric oxide (NO). Endothelial cytotoxicity of homocysteine is modulated by the presence of NO; NO and homocysteine react under physiological conditions to form the non-toxic S-nitroso-homocysteine. Furthermore, NO is an important vascular mediator, released continuously by endothelial cells in the basal state. In the hypercholesterolemic rabbit model, dietary supplementation with L-arginine reduces atheroma formation, improves endothelium-dependent dilation, decreases platelet aggregation and monocyte adherence to aortic endothelium. It has also been shown that L-arginine supplementation inhibits platelet aggregation in healthy young adults via the nitric oxide pathway. In hypercholesterolemic humans, L-arginine supplementation has been shown to improve endothelium-dependent vasorelaxation. Furthermore, nitric oxide, which is known to serve as a negative feedback for vascular endothelial growth factor (VEGF), has an added benefit in preventing angiogenesis and metastasis. Thus, with those known health benefits of continuously released low levels of nitric oxide, in the present invention a high arginine and low methionine containing soy protein is used as a natural approach to detoxify homocysteine and represents a viable and attractive alternative to current therapy of using vitamin supplements. The preparation of this aspect of the invention is discussed in Example 12.

Low Sulfur Amino Acid Protein Ingredient to Reduce the Risks of Cancer and Osteoporosis.

Methionine plays a critical metabolic role in tumor development by ultimately promoting protein synthesis and cell proliferation. Thus, the lower methionine content of soy proteins compared to animal proteins such as casein contributes to the inhibition of tumorigenesis by low methionine proteins such as commercial soy protein isolate (Hawrylewicz, E. and Huang, H., In "Dietary Proteins, How They Alleviate Disease and Promote Better Health", Liepa, G., editor, Amer. Oil Chem. Soc., Champaign, Ill., pp. 123–150, 1992). The use of an even lower methionine containing high BC composition of this invention (Example 12) in high protein food applications will further improve the safety of consuming high protein foods.

The composition of proteins in our diet also influence bone health by influencing our retention of dietary calcium. Higher urinary calcium excretion for subjects on an animal protein diet is related to higher content of sulfur containing amino acids (Breslau, N. et al., J. Clin. Endocrinol. Metab. 66:140–146, 1988) and is related to higher incidence of hip fractures in women who have higher animal intakes (Abelow, B. et al., Calcif. Tissue Int. 50:14–18, 1992). One of the mechanisms involved is as follows: sulfur is oxidized to sulfate in vivo, which generates a fixed acid load that is buffered by bone, resulting in bone dissolution. The low content of sulfur amino acids of a high beta-conglycinin composition that is low in methionine is beneficial in the prevention of osteoporosis, cancer and heart disease.

Functional Food Applications

The above physiological benefits of beta-conglycinin for functional food applications have not been recognized by food product developers. New high beta-conglycinin compositions which are now possible in accordance with the present invention, are used to make beverages and meat and cheese analogs with improved texture, flavor, color and nutritional quality.

Additional Modifications

The present invention includes additional modifications of beta-conglycinin-rich soybeans and beta-conglycinin proteins which further extend the efficiency of isolate manufacture and usefulness of high BC compositions. Examples include the following: 1) Reduction of the amount of non-storage proteins in the soybean to increase the yields of beta-conglycinin; 2) addition of single, double, triple, or quadruple-lipoxygenase-null trait to reduce off-flavor development during manufacture of high beta-conglycinin compositions; 3) reduction in the content of linoleic and linolenic acid in the soybean, for example by increasing oleic and or stearic acid, to reduce off-flavor development during the manufacture of high beta-conglycinin compositions; 4) modify the amounts of alpha, alpha' and beta-subunits of beta-conglycinin to obtain various benefits (e.g. reduce allergenicity, improve solubility) by using overexpression of specific subunits or antisense of specific subunits or modify the structures of particular subunits by using site-directed mutatgenesis; 5) partial enzymatic hydrolysis of the beta-conglycinin-rich isolate using different enzymes and conditions to improve protein solubility, cheese analog properties, gelling and foaming properties; and 6) enzymatic phosphorylation or deamidation of beta-conglycinin proteins to improve solubility and related functional properties.

The high beta-conglycinin, low glycinin soybean is also achieved through genetic engineering. The beta-conglycinin and glycinins are encoded by multiple gene families in soybean. These genes are regulated by transcription factors and other regulatory proteins. Efficient transformation of soybean allows the introduction of sense and antisense genes into the soybean genome. Antisense against the glycinin genes is an effective way of lowering the glycinin level. The appropriate group 1 glycinin cDNA nucleotide sequences can be obtained from soybean seed expression tag (EST) databases and cloned in the antisense orientation in a seed expression cassette. These constructs can be used to generate transgenic soybean plants that can be screened for reduced expression of group 1 glycinin. The group 1 glycinin gene sequences are described by Nielson et al. (Cellular and Molecular Biology of Plant Seed Development, Eds. B. Larkins and I. Vasil Kuwer Academic Publishers, (1997)). Published information or that of EST databases can be used to isolate the group 1 glycinin genes of interest and these genes can be appropriately truncated for co-suppression of group 1 in transgenic soybeans. It is also possible to lower the glycinin level through co-suppression of glycinin gene expression with glycinin promoter or sense glycinin RNA. Transcription factors and other regulatory proteins that control the expression of glycinin can be manipulated to achieve lower glycinin content soybeans. Transcription factors and other regulatory proteins can be identified by map-based cloning using the low glycinin soybean mutant. The reduction of glycinin accumulation in new soybean varieties is likely associated with a simultaneous increase in beta-conglycinin of the low glycinin mutants. One can also increase levels of beta-conglycinin (simultaneously decreasing the levels of glycinin) by overexpressing beta-conglycinin gene-specific transcription factors or other regulatory proteins that have a positive effect, or by antisensing RNA-mediated repression of regulatory proteins that have a negative effect on beta-conglycinin expression. The higher level of a particular beta-conglycinin subunit or subunits can also be achieved by engineering the genes encoding these subunits under the control of seed-specific promoters. This allows the specific increase of the desired beta-conglycinin subunits. Mutant forms of beta-conglycinin that have enhanced functionality can also be engineered in vitro and introduced into soybean using transgenic technology.

Gamma rays can be used to generate a population of soybean mutants. That population can be screened for absence or decrease of the levels of group 1 glycinin proteins in seeds, or physical mutations in group 1 glycinin genes by genetic mapping strategies.

Similar methods can be used to eliminate Kunitz and or Bowman Birk protease inhibitors in high BC soybeans.

Additional procedures and methods are well known in the art. Suitable procedures, materials and methods for antisense technology may be found in Burkle L., Hibberd, J. M., Quick, W. P., Kuhn, C., Hirner, B., Frommer, W. B. Plant Physiol. 118(1):59–68 (1998); Piquemal J, Lapierre C, Myton K, O'Connell, A., Schuch, W., Grima-Pettenati, J., Boudet, A. M. Plant J. 13(1):71–83 (1998); and Temple S. J., Bagga S., Sengupta-Gopalan C. Plant Mol Biol. 37(3):535–47 (1998). Suitable procedures, materials and methods for co-suppression technology may be found in: Palauqui, J. C., Vaucheret, H., Proc. Natl. Acad. Sci. USA. 95(16):9675–80 (1998); Que, Q., Jorgensen, R. A. Dev. Genet. 22(1):100–9 (1998); de Carvalho Niebel, F., Frendo P., Van Montagu, M., Cornelissen, M. Plant Cell 7(3):347–58 (1995).

Suitable procedures, materials and methods related to protein ingredient preparation and use in food applications may be found in Liu, KeShun, Soybeans—Chemistry, Technology and Utilization, Chapman & Hall, NY, (1997); Erickson, D. R., editor, Practical Handbook of Soybean Processing and Utlization, AOCS Press, Champaign, Ill. and United Soybean Board, St. Louis, Mo., (1995); Applewhite, T. H. (ed.) Proceedings of the World Congress on Vegetable Protein Utilization in Human Foods and Animal Feedstuffs, American Oil Chemists' Society, Champaign, Ill. (1989); Soy Protein Products—Characteristics, Nutritional Aspects and Utilization, Soy Protein Council, Washington D.C. (1987); Damodaran, S. and Paraf, Alain, Food Proteins and Their Applications, Marcel Dekker, Inc. NY (1997); Gueguen, J. and Popineau, Y., eds. Plant Proteins from European Crops, Springer-Verlag, NY, 1998; Kolar, C. W., et al., J. Amer. Oil chem. Soc. 56:389–391, (1979); Fukushima, D., Food Rev. Int. 7:323–351, (1991); Hoogenkamp, H. W., Vegetable Protein Technology Value in Meat, Poultry & Vegetarian Foods, (1992); Fox, P. F., Cheese: Chemistry, Physics and Microbiology, Vol. 2, Major Cheese Groups, pp 339–383, (1987); Mead, G. C. 1989, Processing of Poultry, Elsevier Appl. Sci., NY; Forrest, J. C. et al. 1975, Principles of Meat Science, W. H. Freeman Co., San Francisco; Wilson, L. A., Amer. Oil Chem. Soc., (1995), and Hua, Y. F., et al., J.A.O.C.S. 73:1067–1070 (1996), all of which are incorporated herein by reference.

EXAMPLES

The following examples are provided to further illustrate the present invention and are not intended to limit the invention beyond the limitations set forth in the appended claims. Those examples which refer to the use of soy protein isolates are exemplary only and those skilled in the art would know which particular soy protein composition of the present invention could be used in production of the food products described herein.

Example 1

SDS-PAGE Gel Electrophoresis of Soybeans and Soy Protein Isolate

1) Weighed out 5 mg of sample of known protein content determined by kjeldahl, (protein=nitrogen×6.25) and placed it in a 650 microliter microcentrifuge tube.

2) Added SDS sample solubilizing solution (containing 10% glycerol, 2.3% SDS, 0.0626 M Tris pH 6.8, 5% 2-mercaptoethanol, 0.05% Bromophenol Blue) to a final protein content of 4 mg/mL.

3) Seal tubes and in the case of SPI samples placed in shaker for 20 minutes. Placed in boiling water bath for 10 minutes.

4) Cooled samples to room temperature.

5) Spun samples in microcentrifuge (~14,000×g) for 10 minutes.

6) Recovered supernatant.

7) Loaded 5–8 microliters (20–30 micrograms protein). The running/staining conditions:

1) All gels had been analyst-cast 10–20% acrylamide+Bis-acrylamide (T), and 2.67% C (weight of T due to Bis-acrylamide) Laemelli gels that were 0.75 mm thick. The gels were cast and run using the Bio-Rad Protean II xi system which creates gels which are approximately 16 cm×16 cm.

2) Stacking gels were cast with 15 wells, and samples were not run in the outer lanes. Bio-Rad Broad Molecular weight standards were loaded on each side of the gel to be used for apparent molecular weight determination.

3) The gels were run using constant voltage (60–100 volts overnight) or constant current (15–30 mA/gel for 6–8 hours).

4) Gels were fixed in 12.5% trichloroacetic acid for at least 1 hour at room temperature.

5) The gels were removed from TCA and rinsed briefly in deionized water. They were placed in colloidal Coomassie Solution A (11% Ammonium sulfate/2% Phosphoric acid) for 1 hour at room temperature, then placed in staining solution composed of 160 ml of solution A, 40 ml of methanol, and 4.2 ml of solution B (1 gm Coomassie G250 in 20 ml of deionized water).

6) The gels were stained at room temperature in this solution for at least 16 hours (>24 is best), then they were rinsed with deionized water and placed in 7% acetic acid to wash away the trace of background staining that existed. At this point gels were ready for imaging or photography.

Digital images of Coomassie stained gels were generated using a Kodak Videk Mega-plus charge-coupled device (CCD) array camera and scanning software included with a Biolmage Visage 2000 Image analysis system. The CCD array camera generated digital images which are 1024×1024 pixels, with 256 digital values representing a range of optical density. During the image acquisition process, the system was calibrated with regard to pixel size and digital values. The gels were scanned using transmitted light, a 17 mm lens, 2 neutral density filters, and a yellow filter to enhance contrast of the Coomassie stain.

Analysis of the digital images was performed using Biolmage Whole Band analysis software. With this software, the analyst provided lane boundaries, and the software identified bands then generated their boundaries on an automated basis. The analyst had the ability to remove band boundaries which failed to represent the band, and the ability to assist in the determination of boundary placement by indicating the main axes of the band. This method controls analyst bias by applying the same algorithms to the boundary determination process. It was also possible for the analyst to manually define (draw) the band boundary, but this approach was only used where all other approaches failed (typically less than 2% of the bands). The whole band software quantitated individual bands by summing the digital values for all pixels within the band boundary, generating a value known as integrated optical density or IOD. Commercial molecular weight standards (Bio-Rad Broad Molecular Weight Standards Catalog #161-0317) run in individual lanes on the same gel are used to determine the apparent molecular weight of bands in samples. Individual bands may be named by the analyst to aid in their identification on the bandlist.

The results of image analysis were presented in tabular form known as a "bandlist". The bandlist contains data grouped by lanes including the band number (numbered from the top of the lane to the bottom), band name, band IOD, % IOD (% of all quantitated material in the lane represented by this band), and molecular weight. Copies of the computer screen were printed as "screendumps". Screendumps were generated showing the digital gel image with no annotation in place, with centers of quantitated bands indicated by a dashed line, and with full annotation showing land boundaries, lane names, band centers, band boundaries, and molecular weight standards.

Example 2

Median Particle Diameter and Viscosity of Purified, BC, Laboratory Soy Protein Isolate and Commercial Protein Commercial soy protein isolates, Supro 760 (Com'l SPI A) and Supro 940 (Com'l SPI B), were obtained from Protein Technologies International, St. Louis Mo. Commercial soy protein concentrate, Promine DS (Com'l SPC), was obtained from Central Soya company, Inc., Fort Wayne, Ind. Whole protein isolate (Lab. SPI) was prepared according to the method of Boatright, W. L., et al., J. Amer. Oil Chem. Soc. 72:1439–1444, (1995), except petroleum ether was used to extract the fat. Emulsions containing protein (1% protein), peanut oil (10%), sucrose (5% in water phase), NaCl (70 mM, 0.4% in water phase), and CaCl2 where indicated (4 mM) were prepared by sonication (160 watts, 60 sec.) and median particle diameter measurements were determined using a Malvern mastersizer laser light diffraction instrument. A Bohlin VOR rheometer was used to determine the viscosity of heat-treated samples (14.6 1/sec. shear rate, 5 min., 5 degrees C.). The emulsions were frozen (4 days, −14 degrees C.) and thawed or heat-treated (20 mL in glass vial submerged in 90 degrees C. water bath for 60 minutes).

The small particle diameters of the heat-treated or frozen-thawed emulsions prepared with sodium caseinate and beta-conglycinin demonstrate the potential of beta-conglycinin for replacing sodium caseinate in emulsion applications near pH 6.7, such as nutritional beverages and coffee creamers as shown in Table 1.

TABLE 1

Median particle diameters of emulsions stabilized by purified beta-conglycinin, laboratory soy protein isolate and commercial protein ingredients.

| | Median Particle Diameter (micron) | | | |
|---|---|---|---|---|
| | 0.4% NaCl | | 0.4% NaCl, 4 mM CaCl2 | |
| Protein | pH 6.0–6.1 | pH 6.6–6.8 | pH 6.0–6.1 | pH 6.6–6.8 |
| Sodium Caseinate | 1.0 | — | 1.1 | 1.1 |
| Beta-conglycinin | 1.2 | 1.2 | 9.8 | 3.4 |
| Lab. SPI | 14.2 | 2.2 | 36.3 | 14.1 |
| Com'l SPI A | 30.0 | 1.6 | 69.1 | 61.9 |
| Com'l SPI B | 82.7 | 56.0 | 89.2 | 81.8 |
| Com'l SPC | 46.6 | 44.6 | 49.7 | 60.4 |

TABLE 2

Median particle diameter or heat-treated and freeze-thawed emulsions stabilized by purified beta-conglycinin, laboratory soy protein isolate and commercial protein ingredients, 0.4% NaCl, 5% sucrose.

| | Median Particle Diameter (micron) | | | |
|---|---|---|---|---|
| | Heat-treated | | Freeze-thawed | |
| Protein | pH 6.0–6.1 | pH 6.6–6.8 | pH 6.0–6.1 | pH 6.6–6.8 |
| Sodium Caseinate | 1.0 | — | 1.0 | — |
| Beta-conglycinin | 3.1 | 1.4 | 4.0 | 13.8 |
| Lab. SPI | 39.1 | 11.5 | 55.0 | 88.0 |
| Com'l SPI A | 34.9 | 1.9 | 83.9 | 75.3 |
| Com'l SPI B | 72.4 | 49.9 | 111 | 104 |
| Com'l SPC | 47.7 | 49.9 | 111 | 98.8 |

TABLE 3

Viscosity of heat treated emulsions stabilized by purified beta-conglycinin, laboratory soy protein isolate and commercial protein ingredients, 0.4% NaCl, 5% sucrose.

| | Protein | | | | |
|---|---|---|---|---|---|
| pH | Beta-conglycinin mPa s | Lab. SPI mPa s | com'l SPI A mPa s | Com'l SPI B mPa s | Com'l SPC mPa s |
| 6.6 | 50 | 180 | 60 | 70 | 230 |
| 6.1 | 60 | 650 | 270 | 50 | 140 |
| 5.6 | 1,490 | 270 | 110 | 30 | 110 |
| 5.0 | 120 | 30 | 70 | — | 100 |

Example 3

Pilot Plant Preparation of High BC-SPI, Low BC-SPI and Cntrl-SPI

A. Removal of Fat from Soybeans

1. Adjust soybeans to about 10% moisture and temper at room temperature.

2. Crack soybeans by using a cracking mill.

3. Dehull the cracked soybeans by using a Kice Aspirator.

4. Condition the cracked and dehulled soybeans at 50–60 degrees C. by using a cooker.

5. Flake the conditioned soybeans using a Flaking Mill.

6. Extract soybean flakes with hexane.

7. Desolventize the defatted soybean meal in a laboratory fume hood for three days.

8. Flakes from step 7 were ground to make flour used in section C below.

B. SPI-acid-hb and Steps 1 and 2 for SPI-UF-hb

BC-SPI-acid-hb (acid hb=heat before acid precipitation) and low BC-SPI-acid-hb were processed as described below. Cntrl-SPI-acid-hb used the process outlined in section C below except the protein of C2 was adjusted to pH 7.0 and heat-treated (72 degrees C., 15 sec.) before C3. There was no heat-treatment in C6.

1. Water was added to a 200 liter jacked tank and adjusted to 27–35 degrees C. and pH 8.5–9.0 using 20% NaOH. Defatted soybean flakes were added and mixed with an agitator equipped with two propellers and a powered in-line 3-stage mixer which was fitted with fine, medium and coarse rotors. The powered in-line mixer with a closed loop circulation was used throughout the extraction process to reduce the particle size of the flakes and improve protein extraction. The water to soy flour ratio was 10/1 (w/w). The pH of the slurry was readjusted to pH 8.5–9.0 if pH of the slurry is below 8.5.

2. The solubilized soy protein was recovered from the extraction slurry by centrifuging (25–35 degrees C.), first with a decanter to remove the majority of the spent solids, followed by clarification of protein-containing liquid in a desludging disk centrifuge at a feed rate of 250–500 kg/h.

3. The pH of the clarified protein solution was adjusted to 6.8–7.0 using 6% hydrochloric acid. The protein solution was heat-treated at 72 degrees C. for 15 seconds or at 90 degrees C. for 20 seconds using a plate and frame heat exchanger and cooled to 25–35 degrees C.

4. The pasteurized protein solution was adjusted to pH 4.5+/−0.1 by adding hydrochloric acid (12%) and allowed to react for 30 minutes at 30–35 degrees C.

5. The precipitated protein was recovered using a desludging disk centrifuge at a feed rate of 200–400 kg/h and desludging interval of 3 minutes.

6. The protein curd was washed for 10–30 minutes, two times using acidified water (pH 4.5+/−0.1, 30–35 degrees C.). Ratio of washing water to packed wet solids was 5:1 (w/w). Any lumps in the curd were broken up using a powered in-line mixer. The protein curd was recovered using a desludging disk centrifuge at a feed rate of 350–450 kg/h after each washing.

7. The washed curd was mixed with dilute sodium hydroxide (0.5%) to neutralize (pH 7.0–7.2), diluted with water to 12–15% solids (preferably 15% solids) and readjusted to pH 7.0–7.2. A powered in-line mixer homogenizes the slurry before spray-drying. The protein solution was stored at 4 degrees C. or as cool as possible before spray drying using a heat exchanger.

8. The neutralized and homogenized protein solution was adjusted to 45–55 degrees C. and was spray dried using an inlet air temperature of 180–185 degrees C., outlet air temperature of 85–90 degrees C.

C. SPI-acid-ha

1. Water was added to a 300 liter jacked tank and adjusted to 55 degrees C. and pH 9.0–9.5 using 30% NaOH. Defatted soybean flour was added and mixed with a propeller-type mixer set at high speed setting (1725 rpm). The water to soy flour ratio was 12/1 (w/w). Extraction time was 45 minutes.

2. The solubilized soy protein was recovered from the extraction slurry by using a desludging disk centrifuge at a feed rate of 250–500 kg/h.

3. The clarified protein solution was adjusted to pH 4.5+/−0.1 by adding hydrochloric acid (30%) and allowed to react for 30 minutes at 45 degrees C.

4. The precipitated protein was recovered using a desludging disk centrifuge at a feed rate of 200–400 kg/h and desludging interval of 3 minutes.

5. The protein curd was washed for 10–30 minutes, two times using acidified water (pH 4.5+/−0.1, 30–35 degrees C.). Ratio of washing water to packed wet solids was 6:1 (w/w). The protein curd was recovered using a desludging disk centrifuge at a feed rate of 350–450 kgk/h after each washing.

6. The washed curd was mixed with sodium hydroxide (30%) to adjust pH (pH 7.2) and then heat treated at 72 degrees C. for 15 seconds or 90 degrees C. for 20 seconds using a plate and frame heat exchanger and cooled to 25–35 degrees C. Then the pH was adjusted to pH 6.8 using HCl (30%).

7. The protein solution was adjusted to 45–55 degrees C. and was spray dried using an inlet air temperature of 204–215 degrees C., outlet air temperature of 88 degrees C.

D. Ultrafiltration and Diafiltration

1. Clarified protein solution was obtained from step 2 of Example 3B or 3C above. To make SPI-UF-hb (hb=heat before), the protein solution was neutralized (pH 6.8–7.0) and heat treated to 72 degrees C. for 15 seconds or 90 degrees C. for 20 seconds using a plate and frame heat-exchanger. To make SPI-UF-ha (ha=heat after), the protein solution (pH 9.0) was used from step 2 and the sample was neutralized and heat-treated after step 4.

2. The protein solution was passed over an ultrafiltration membrane (e.g. hollow fiber) with a molecular weight cutoff of 100,000 Daltons. The original volume of the protein solution was maintained in a feed container during ultrafiltration and diafiltration by adding water to make up for the removed permeate.

3. The retentate solution was recycled to the feed container.

4. Once the permeate was about 1.3 to 1.5 times the original feed volume, the addition of water to the feed container was discontinued and the permeate was collected.

5. The volume of the feed container was reduced by ultrafiltration until a solids content of about 15% solids was achieved and adjusted to pH 6.8–7.0 by adding 8% NaOH or 6% HCl.

6. The retentate was spray dried using an inlet air temperature of 180–185 degrees C. and outlet air temperature of 85–90 degrees C.

Example 4

Composition, Solubility and Color of Soybeans and BC-SPI Materials

BC-SPIs, Low-BC SPI, and Cntrl-SPIs were made by acid precipitation and ultrafiltration methods at POS Pilot Plant Corp., Saskatoon, SK, Canada and at Texas A&M University, College Station, Tex., according to the methods in Example 3. The manufacture of BC-SPI-UFpH9 included an addition of sodium tripolyphosphate (0.5% based on the weight of the defatted flakes) in the SPI extraction solvent (pH 8.5–9.0), possibly accounting for the higher ash content of the SPI (Table 5). Com'l SPI A, C (partially hydrolyzed) & D were obtained from Protein Technologies International, St. Louis, Mo. Com'l SPI D, E and F were obtained from Archer Daniel Midland, Decatur, Ill. Sodium caseinate (Alanate 180) was from New Zealand Milk Products (North America) Inc., Santo Rosa, Calif. Compositions and physical properties of the SPIs are presented below.

Protein composition: Total protein in SPIs were determined by combustion (Official Methods of Analysis of the AOAC, 16$^{th}$ Edition, 1995; 990.02, Locator#4.2.08). The amount individual types of proteins in SPIs were determined as a percentage of the total protein using gel electrophoresis (Example 1).

BC-SPI contained approximately twice as much BC compared to Com'l SPI-A (Table 6). Only the beta-subunit of beta-conglycinin was present in low-BC SPI.

Fat composition: The amount of fat in SPIs was determined by an acid hydrolysis method (Official Methods of Analysis of the AOAC, 1995, 16$^{th}$ Ed., Method 922.06 (modified) Locator#32.1.14).

Trypsin inhibitor activity: Soybeans and SPI were analyzed for trypsin inhibitor activity using a standard AACC method (1995, 9th edition, method 71-10).

Nitrogen solubility index: A portion of sample is suspended in water, with stirring, at 120 rpm and 30 degrees C., for two hours; then diluted to a known volume with water (5 g/250 mls, 2%). A portion of sample extract is centrifuged (1500 rpm) and an aliquot analyzed for Kjeldahl protein. A separate portion of sample is analyzed for total protein. Water soluble nitrogen as a percent of total nitrogen, is defined as nitrogen solubility index (Official and Tentative Methods of the AOCS (1989), 4$^{th}$ Edition, Method Ba 11-65).

SPI color: A sample of SPI was placed in a Hunter Colorimeter (Hunter Associates Laboratory, Inc., Reston, Va.) where color reflectance is measured against three scales on the instrument: L, a, and b (Am. Assoc. Cereal Chemists, Method 14-22). Ultrafiltrated BC-SPI of the invention had significantly higher whiteness and lower yellowness than other SPIs and were therefore more similar in color to commercial sodium caseinate (Alanate 180) (Table 4).

Size of hydrated SPI particles: Protein isolate powder was placed directly in water circulating in the Horiba LA910 particle size analyzer in the amount necessary to obtain a light transmitant percentage of 70% to 90%. Every sample was mixed for 10 minutes in the instrument with agitation speed of 2 and circulation speed of 2 (peristaltic pump.) Particle size was determined using a relative (to water) refractive index of 1.02-ooi.

BC-SPI-acid-ha of the invention were the only unhydrolyzed SPIs which upon dispersion in water had less than 15 percent of the particle volume contributed by particles greater than 10 microns (Table 4).

TABLE 4

Nitrogen solubility index (NSI), color and particle size distribution of the BC-SPIs compared to control and commercial isolates.

| Protein isolates | NSI % | Hunter colorimeter values L (whiteness), b (yellowness) | | P. Vol >10 m.* % | Med.** Microns |
|---|---|---|---|---|---|
| Sodium caseinate | 98 | 92.4 | 7.1 | 0.0 | 0.30 |
| BC-SPI-acid-ha, 72 C. | 96 | 86.1 | 10.9 | 7.3 | 0.37 |
| BC-SPI-acid-ha, 90 C. | 95 | 85.9 | 11.3 | 6.9 | 0.38 |
| Cntrl SPI-acid-ha, 72 C. | 94 | 86.1 | 10.9 | 19.7 | 0.39 |
| Cntrl SPI-acid-ha, 90 C. | 94 | 86.1 | 11.0 | 18.3 | 0.31 |
| Cntrl SPI-UFpH9-ha | — | 85.2 | 10.6 | 11.0 | 0.37 |
| BC-SPI-UF-hb, 72 C. | 96 | 89.3 | 8.3 | 9.9 | 0.30 |
| BC-SPI-acid-hb, 72 C. | 34 | 85.5 | 11.8 | 30.8 | 1.32 |
| Cntrl SPI-acid-hb, 72 C. | 95 | 85.2 | 11.5 | 19.4 | 0.35 |
| Cntrl SPI-acid-hb, 90 C. | 63 | 83.5 | 12.8 | 75.1 | 53.2 |
| Com'l SPI A (S760) | 63 | 85.5 | 15.4 | 74.4 | 65.8 |
| Com'l SPI C (S670) | 82 | 82.8 | 13.5 | 0.9 | 0.37 |
| Com'l SPI D (S500E) | 72 | — | — | 84.0 | 72.2 |
| Com'l SPI E (P974) | 67 | 85.8 | 12.6 | 92.0 | 96.6 |
| Com'l SPI F (A.DHV) | 78 | 86.1 | 11.4 | 76.7 | 71.5 |

*p Vol >10 m. - particle volume from particles greater than 10 microns
**Median particle diameter
hb = heat-treated before UF or acid precipitation
ha = heat-treated after acid precipitation

TABLE 5

Chemical composition of protein isolates. Protein is expressed as nitrogen × 6.25 (likely over represents total soy protein).

| SPI | Protein %, dry basis | Fat (acid hydrolysis %, dry basis | Ash %, dry basis |
|---|---|---|---|
| Na Caseinate | 95.74 | 0.75 | 3.71 |
| Low-BC-SPI-hb | 94.39 | 4.02 | 3.89 |
| BC-SPI-acid-hb | 91.89 | 4.57 | 3.86 |
| BC-SPI-acid-ha | 95.24 | 2.54 | 3.75 |
| BC-SPI-UFpH7-hb | 92.31 | 3.18 | 3.65 |
| BC-SPI-UFpH9 | 88.39 | 3.57 | 5.83 |
| Cntrl-SPI-UFpH9-ha | 92.28 | — | — |
| Cntrl-SPI-acid-hb | 93.03 | 3.05 | 4.60 |
| Cntrl-SPI-acid-ha | 92.34 | — | — |
| Com'l SPI A | 92.55 | 4.94 | — |

TABLE 6

Protein composition of SPI's. BBI = Bowman Birk protease inhibitor; KTI = Kunitz protease inhibitor.

| Soy protein isolates | SPI protein composition (% of protein) | | | | | Protease inhibitor Activity (TIU/mg prot.) |
|---|---|---|---|---|---|---|
| | BC | Glycinin | A$_3$ | BBI | KTI | |
| Low-BC-SPI-acid-hb | 12.4* | 55.2 | 5.7 | — | 2.4 | 31.5 |
| BC-SPI-acid-hb | 51.3 | 5.5 | 2.4 | 0.50 | 2.5 | 85.2 |
| BC-SPI-acid-ha | 61.9 | 3.0 | 1.8 | 0.35 | 2.8 | 45.6 |
| BC-SPI-UF pH7-hb | 54.0 | 4.2 | 1.8 | 2.4 | 3.1 | 284.6 |
| BC-SPI-UFpH9 | 40.0** | 3.4 | 1.5 | 3.1 | 3.7 | 347.7 |
| Cntrl-SPI-UF pH9-ha | 28.2 | 45.4 | 5.9 | 0.0 | 2.4 | 28.3 |
| Cntrl-SPI-acid-hb | 30.0 | 37.4 | 5.9 | 0.31 | 1.7 | 26.8 |
| Com'l SPI A | 26.1 | 45.2 | 5.2 | 0.17 | 0.7 | 8.9 |
| Com'l SPI E | 28.9 | 39.8 | 4.9 | 0.37 | 2.5 | 10.0 |
| Com'l SPI F | 28.3 | 45.5 | 5.4 | 0.31 | 2.1 | 10.7 |

*Represents beta-subunit of BC. There were no alpha or alpha-prime subunits of BC in low-BC-SPI.
**A broad band near 62 kDa (8.2% of total protein) likely represents hydrolysis products of alpha and alpha' subunits of BC, but was not included in the calculation for BC here.

TABLE 7

Protein composition of soybeans. Growing regions of High BC soybeans were IL = illinois, PR = Puerto Rico.

| Soybean | Beta-conglycinins (% of protein) | Glycinins (% of protein) | BBI (% of protein) | KTI (% of protein) | Trypsin Inhibitor Activity (TIU/mg protein) |
| --- | --- | --- | --- | --- | --- |
| High BC-IL | 53.0 +/- 0.9 | 2.8 +/- 0.7 | 2.9 +/- 0.1 | 3.5 +/- 0.4 | 92.4 +/- 3.3 |
| High BC-PR | 51.6 +/- 0.2 | 1.6 +/- 0.1 | 2.6 +/- 0.4 | 3.7 +/- 0.3 | 77.4 +/- 2.2 |
| Com'l (H6397) | 26.9 | 36.6 | 0.9 | 3.2 | 31.2 |
| Com'l soybeans* | — | — | — | — | 31.8 +/- 4.4 |

*Average of 6 varieties (Hartz 6397, 6061, 5488, 6255, 616, 5088)

TABLE 8

Isoflavone content of SPIs. The total isoflavones values listed are the sums of the individual isomers of genistein, daidzein and glycitein, normalized for their molecular weight differences to give the total isoflavone concentrations

| | Isoflavone composition of SPIs (micrograms/g dry SPI) | | | |
| --- | --- | --- | --- | --- |
| Isoflavones | BC-SPI-acid-hb | Low-BC-acid-hb | Cntrl SPI-A | Cntrol-SPI-acid-hb |
| Malonyl daidzin | 86 | 31 | 0 | 0 |
| Malonyl glycitin | 25 | 34 | 88 | 26 |
| Malonyl genistin | 300 | 150 | 819 | 204 |
| Daidzin | 47 | 67 | 190 | 579 |
| Glycitin | 17 | 32 | 60 | 69 |
| Genistin | 200 | 170 | 658 | 1259 |
| Acetyl daidzin | 17 | 0 | 207 | 0 |
| Acetyl genistein | 41 | 31 | 255 | 28 |
| Acetyl glycitin | 0 | 0 | 18 | 0 |
| Daidzein | 106 | 92 | 84 | 191 |
| Glycitein | 21 | 35 | 21 | 30 |
| Genistein | 290 | 217 | 116 | 273 |
| Total Daidzein | 188 | 148 | 315 | 544 |
| Total Genistein | 594 | 418 | 1099 | 1181 |
| Total Glycitein | 45 | 73 | 116 | 88 |
| Total Isoflavones | 827 | 639 | 1530 | 1813 |

Example 5

Cholesterol and Triglyceride Lowering Properties of BC-SPI

Animals and diets: Adult hamsters (male Golden Syrian) (94+/-5.5 g.) were housed individually in wire bottomed stainless steel cages in an environmentally controlled room at 23 degrees C. with an alternating 12-h light:dark cycle. Upon arrival, hamsters were fed powdered nonpurifed diet rodent chow (Purina, St. Louis, Mo.) for 1 week to acclimate them to the powder diets. Hamsters were randomly assigned to one of five dietary treatment groups (n=10 per group). Diets were similar except for the source of protein (table 1). Na Caseinate was Alanate 180, received from New Zealand Milk Products. Low-BC soybeans were obtained from Asgrow seed company (A233) and were processed to make low-BC-SPI-acid-hb (Example 3B). The control-SPI and BC-SPI were described previously. All hamsters were fed ad libitum for 6 weeks and food intake was monitored during weeks 1, 3 and 6. Retro-orbital blood samples were collected on days 0, 14, 28 and 42 for measurements of serum lipids (Table 10). At the end of the study the hamsters were sacrificed by exsanguination and liver was obtained to measure liver lipid levels.

Cholesterol and triglyceride assays: Total and HDL cholesterol concentrations were measured enzymatically using commercial kits (Wako Cholesterol CII Enzymatic Kit (Cat. No 276-64909), Sigma HDL (Cat. No. 352-3). Triglycerides were determined using Sigma triglycerides kit (Cat. No. 337). VLDL and LDL concentrations were calculated as the difference between total and HDL cholesterol. In addition, the serum lipoprotein cholesterol profiles were directly determined by pooling the hamster serum from each group and separating the lipoproteins on 2 Superose 6 columns (Pharmacia, Uppsala, Sweden) according to the procedure described by E. S. Krul et al. (Arteriosclerosis 9: 856–868, 1989).

Fecal bile acids and neutral sterol assays: Fecal bile acids were extracted from dried feces by the method of Van der Meer et al. (Van der Meer et al. In: Cholesterol Metabolism in Health and Disease: Studies in the Netherlands. Wageningen:Ponsen and Locijen, 113–119, 1985). Extracted bile acids were assayed as described by Turley and Dietschy (Turley S D and Dietschy J M, J. Lipid Res. 19: 924–928, 1978). Fecal neutral sterols were extracted from dried feces according to the method of Grundy et al. (Grundy S M et al. J. Lipid Res. 6: 397–410, 1965). Extracted, non-derivatized sterols were analyzed on a Hewlett Packard Model 6890, using a HP-5 Ultra 2 glass capillary column (50 m×0.32 mm I.D.).

TABLE 9

| Basal diet composition | |
| --- | --- |
| Component | g/100 g |
| Protein* | 22 |
| Rice flour | 43 |
| Oil mix** | 12 |
| Cellulose | 7.5 |
| Mineral mix | 3.5 |
| Vitamin mix | 1.0 |
| Wheat Bran | 7.5 |
| Choline chloride | 0.3 |
| Potassium bicarbonate | 2.0 |
| Cholesterol | 0.1 |

*protein value based on 6.25 × nitrogen.
**cocoa butter (25%), flax seed oil (3%), palm oil (35%), safflower oil (19%), sunflower oil (85% oleic; 18%)

TABLE 10

Composition of hamster serum and feces lipids measured after 6 weeks on diets containing soy protein isolates and food intake after 5 weeks.

| | Serum lipids | | Fecal | | Fecal | Hepatic | Food |
|---|---|---|---|---|---|---|---|
| SPI | Cholesterol (mg/dl) | Triglycerides (mg/dl) | Cholesterol (ug/g.dry wt./day) | Fecal Bile Acids (umoles/g dr wt) | Coprostanol (ug/g dry wt/day) | Cholesterol (mg/g liver wt) | Intake (g./day) |
| Na caseinate | 307.2 +/− 30.1 | 243.0 +/− 130.6 | 144 +/− 14 | 0.42 +/− 0.64 | 354 +/− 53 | 3.89 +/− 1.28 | 8.39 +/− 0.73 |
| Com'l SPI A | 262.4 +/− 25.2 | 115.0 +/− 46.7 | 147 +/− 4 | 2.27 +/− 1.18 | 455 +/− 23 | 2.70 +/− 1.15 | 9.17 +/− 1.08 |
| Cntrl-SPI-acid-hb | 248.2 +/− 20.7 | 123.2 +/− 57.7 | 195 +/− 14 | 1.09 +/− 1.09 | 484 +/− 36 | 2.23 +/− 0.27 | 8.48 +/− 0.91 |
| Low-BC-SPI-acid-hb | 248.2 +/− 25.8 | 105.6 +/− 29.0 | 160 +/− 5 | 1.72 +/− 1.11 | 467 +/− 31 | 2.29 +/− 0.51 | 8.92 +/− 0.79 |
| BC-SPI-acid-hb | 222.0 +/− 31.7 | 64.6 +/− 19.7 | 227 +/− 45 | 2.13 +/− 1.06 | 364 +/− 29 | 2.33 +/− 1.13 | 7.40 +/− 0.95 |

Example 6

Properties of BC-SPIs Compared to Commercial SPIs and Sodium Caseinate in a Model Beverage System Materials: BC-SPIs, Cntrl-SPIs and Com'l SPIs are described in Examples 3 and 4.

Emulsion formation: Protein (final concentration of 1%, using 5.71×nitrogen for soy proteins and 6.38×nitrogen for casein) (Morr, C. J., Food Sci. 47:1751, 1982) was slowly added to a 5% sucrose solution using a Dispermat mixer and 0.4% NaCl (in water phase) was added to the mixture. The initial pH of the solutions were adjusted according to the previous experiments so that the final pH of the solution matched the targeted pH. Peanut oil was slowly added to the protein solution in the Dispermat (about 3 minutes) (total formulation weight was 50 g.). The formulations were sonicated (160 watts) for 1 minute in a 50 ml plastic beaker with sonication probe at a depth of the 20 ml mark in the beaker.

Heat-treatment: Protein-stabilized emulsions (20 mL) were transferred to glass vials with screw top lids, submerged in 90 degrees C. water bath for 30 minutes and stored in a refrigerator overnight.

Particle size and viscosity measurements: Samples were tested for viscosity using a Bohlin rheometer (C14 cup and serrated bob, 5 minute equilibrium time, 5 degrees C., 14.6 1/second shear rate, 5 minutes of shear), and were tested for median particle diameter using a Horiba LA910 particle size analyzer (volume basis, relative refractive Index of 1.10, lowest circulation speed.

Results: Sodium caseinate is a good emulsifier and is stable against aggregation as illustrated by the small median particle diameters (0.8 microns) of the emulsions prepared under various conditions of temperature, calcium concentration and pH (Table 11). These desirable properties of sodium caseinate were matched most closely by BC-SPI-acid-ha ingredients (Table 11). Only sodium caseinate and BC-SPI-acid-ha created small emulsion particles in the presence of 4 mM $CaCl_2$. The small sizes of the emulsions stabilized by sodium caseinate and BC-SPI-acid-ha ingredients in the presence 4 mM $CaCl_2$ prevented separation of serum during storage, in contrast to emulsions stabilized by BC-SPI-acid-hb and Com'l-SPI A which had larger particle diameters and exhibited 5 ml and 10 ml of free serum after 1 day (pH 6.7, 0.4% NaCl, 4 mM $CaCl_2$). BC-SPI-acid-ha was also more stable against aggregation reactions than other SPIs at pH 6.5 as illustrated by the small median particle diameter of the emulsions (0.8 microns compared to>1.0 microns for all other SPIs) (Table 11). Both BC-SPI-acid-ha and BC-SPI-acid-hb were much more stable against aggregation during freeze-thaw conditions than commercial SPIs as indicated by the smaller diameters of emulsion particles stabilized by BC-SPIs (2.0–3.7 microns compared to 9.6–97.6 microns). Part of the stability of the BC-SPI-acid-ha could be attributed to the process used to make the ingredient, rather than purely due to the content of beta-conglycinin, because the emulsion particles stabilized by control SPIs also had suprisingly good freeze-thaw stability.

TABLE 11

Median particle diameters of protein-stabilized emulsions prepared or stored under pH, salt and freezing conditions indicated. All emulsions contained 0.4% NaCl and 5% sucrose in the water phase and 1% protein, 10% peanut oil. Results are averages of duplicate tests.

| | Mean Particle Diameter (Microns) | | | | | |
|---|---|---|---|---|---|---|
| Protein | pH 6.7 (microns) | pH 6.5 (microns) | pH 6.7, Freeze-thaw (microns) | pH 6.7, 4 mM Ca (microns) | pH 6.7, 90 C. 30 min (microns) | pH 6.5 90 C. 30 min (microns) |
| Sodium caseinate | 0.8 | 0.8 | 0.8 | 0.8 | 0.8 | 0.7 |
| BC-SPI-acid-ha 72 C. | 0.9 | 0.8 | 2.0 | 1.2 | 0.9 | 0.9 |
| BC-SPI-acid-ha 90 C. | 0.9 | 0.8 | 2.9 | 1.1* | 0.9 | 0.9 |
| Ctrl SPI-acid-ha 72 C. | 1.1 | 1.3 | 1.8 | 12.9 | 1.7 | 1.4 |
| Ctrl SPI-acid-ha 90 C. | 1.1 | 1.6 | 1.9 | 13.6 | 2.8 | 2.9 |
| BC-SPI-UF pH7-hb | 1.3 | 4.9 | 3.3 | 10.6 | 5.1 | 10.6 |
| BC-SPI-acid-hb 72 C. | 1.7 | 2.9 | 3.7 | 19.8 | 4.6 | 6.5 |
| Com. SPI-A | 1.8 | 7.7 | 86.9 | 36.7 | 4.3 | 9.7 |
| Com. SPI-C | 11.8 | 17.5 | 9.6 | 33.8 | 19.3 | — |
| Com. SPI-E | 1.0 | 1.1 | 34.8 | 18.0 | 1.0 | 1.4 |
| Com. SPI-F | 1.1 | 3.7 | 97.6 | 19.1 | 1.8 | 6.6 |

*When this emulsion (20 mL) was heat-treated in a 90 degree C. water bath for 30 minutes, and allowed to cool in a refrigerator, the particle diameter only increased to 2.4 microns. The heat-treated emulsion showed no serum separation after storage (24 hours).

Example 7

Texturizing Properties of BC-SPIs Under Conditions Modeling an Emulsified Meat System Materials:BC-SPIs and Com'l SPIs A, D, E and F are described in Examples 3&4. Com'l SPI A, like Com'l SPI D, is likely manufactured as a highly denatured SPI as measured by the enthalpy of total denaturation (Arrese, E., et al. J. Agric. Food Chem. 39:1029–1032, 1991). To make a high BC composition which is highly denatured, BC-SPI-acid hb and BC-SPI-UFpH7-hb dispersed in water, were transferred to glass vials and submerged in a 90 degrees C. water bath for 30 minutes and then cooled in a refrigerator. Com'l-SPI A was also processed by the same method (90 degrees C. for 30 minutes) to determine how further heat-treatment affected the properties of Com'l-SPI A. Dried egg white was from Canadian Inovatech Inc., Abbotsford, British Columbia.

Emulsion formation: Protein (final concentration of 2%, using 5.71×nitrogen for soy proteins and 6.25×nitrogen for egg white protein) was slowly added to a 5% sucrose solution using a Dispermat mixer and 3.5% NaCl (in water phase) was added to the mixture. The initial pH of the solutions were adjusted according to the previous experiments so that the final pH of the solution matched the targeted pH. Peanut oil was slowly added to the protein solution in the Dispermat (about 3 minute). The formulations were sonicated (160 watts) for 20 second or 1 minute in a 50 ml plastic beaker with sonication probe at a depth of the 20 ml mark in the beaker.

Gelation: Each emulsion sample (20 mL portion) was heated in a glass vial in a 70 degrees C. water bath for 30 minutes or in an 80 degrees C. water bath for 30 minutes, then stored in a refrigerator (5 degrees C.) over night. The time for the emulsions to come to the bath temperatures were approximately 8–10 minutes.

Particle size and viscosity measurements: Samples were tested for viscosity using a Bohlin rheometer (C14 cup and serrated bob, 5 minute equilibrium time, 5 degrees C., 14.6 1/sec. shear rate, sec. and 5 min. of shear), and were tested for median particle diameter using a Horiba LA910 particle size analyzer (volume basis, relative refractive index of 110, lowest circulation speed).

Results: Egg white is an excellent gelling agent used in numerous foods including meat products such as surimi (crab leg analogs). However, like meat protein, egg white is expensive compared to soy protein. The soy protein ingredients which came closest to performing like egg white, under conditions which mimic an emulsified meat system, were the high heat BC-SPIs (Table 14). An explanation is as follows: High heat BC-SPI was made at approximately pH 7.0 and 90 degrees C. where protein denaturation occurs and aggregation of the denatured proteins is limited. The highest viscosities (or firmness, or related water and fat binding) occurs when denatured protein is exposed to conditions which are optimum for the formation of fine gel/aggregate structures. This gelling condition is near pH 5.6–6.0 for BC and gelation of BC can occur at lower temperatures (at or below the denaturation temperature of native BC) when BC is predenatured. Low-heat BC-SPIs were tested for comparison with high heat BC-SPIs. The difference between the viscosities of the samples made with low-heat BC-SPIs and those made with high-heat BC-SPI quantify the value added by predenaturing the soy proteins using a high heat treatment. There is less value added by preheating normal SPI because glycinin forms complexes with BC changing the nature and quantity of subsequent gel-forming reactions (e.g., optimum gelling conditions are moved to different pH values and there are fewer non-aggregated sites on BC available for gel formation).

The emulsifying and thickening properties of BC-SPI ingredients were also compared under low shear conditions (20 seconds sonication rather than 60 seconds). BC-SPI-acid-ha stabilized smaller fat droplets and, after heat-treatment of the emulsion, formed greater viscosities than commercial soy protein isolates (Table 15).

TABLE 14

Viscosities (in units of mPa s) of the heat-treated emulsions prepared with BC-SPIs compared to those prepared with commercial soy protein isolate, pH 5.8, 3.5% NaCl in water, 5% sucrose in water. All emulsions before heat-treatment median particle diameters between 0.9 and 1.1 microns.

| Protein isolate | Viscosity (70° C.) 5 sec shear | Viscosity (70° C.) 5 min. shear | Viscosity (80° C.) 5 sec. shear | Viscosity (80° C.) 5 min. shear |
|---|---|---|---|---|
| Egg white | 464 (17) | 327 (14) | 1800 (375) | 1157 (287) |
| High heat BC-SPI UFpH7-hb | 222 (21) | 189 (13) | 341 (10) | 278 (3) |
| High heat BC-SPI-acid-hb | 229 (17) | 199 (6) | 404 (32) | 317 (9) |
| BC-SPI UFpH7-hb | 149 | 138 | 229 | 202 |
| BC-SPI-acid-hb | 142 | 126 | 193 | 167 |
| "High heat" Com'l SPI A | 74 (4) | 73 (4) | 149 (25) | 145 (6) |
| Com'l SPI A | 115 (0) | 111 (3) | 185 (4) | 164 (3) |

Figures in parentheses indicate standard deviation values for duplicate tests.

TABLE 15

Median particle diameters of protein-stabilized emulsions and viscosities of heat-treated emulsions prepared with BC-SPI and commercial isolates. All emulsions were prepared using 20 seconds of sonication and contained 3.5% NaCl and 5% sucrose in the water phase, 2% protein, 10% oil, pH 5.8. Viscosity values were recorded after 5 minutes of shear.

| Protein isolate | Particle size (microns) | Viscosity (mPa s) 70 C. |
|---|---|---|
| BC-SPI-acid-ha, 72 C. | 1.6 | 27 |
| BC-SPI-acid-ha, 90 C. | 1.6 | 32 |
| BC-SPI-UF-hb, 72 C. | 1.6 | 57 |
| Cntrl-SPI-acid-ha, 72 C. | 1.9 | 43 |
| Cntrl-SPI-acid-ha, 90 C. | 2.2 | 58 |
| Com'l SPI D | 2.0 | 14 |
| Com'l SPI E | 1.9 | 11 |
| Com'l SPI F | 2.8 | 12 |

Example 8

Heat-Induced Gels Near pH 5.6 and Low NaCl in Water Phase

Sample preparation: SPI (described in Examples 3 and 4) suspensions were prepared at 7% protein and 3.5% NaCl in the water phase and allowed to hydrate over night in the refrigerator. Then the pH of the solutions were adjusted to pH 5.6 using dilute HCL.

Dynamic viscoelastic measurements: The storage modulus G', was determined using a Bohlin VOR rheometer. The cell had been previously maintained at 30 degrees C. The sample solution was added to the test cell, covered with mineral oil to prevent evaporation, and subjected to shear oscillation of 1 Hz frequency and 0.025 strain (C14 cup and serrated bob). The temperature was increased from 30 to 70 or 90 degrees C. then lowered to 20 degrees C. at 1 degree C./minute.

Results: The gel-forming properties of BC-SPI-acid-ha ingredients under the conditions tested were much greater than that of control SPIs (4.6–8 fold difference in G') and commercial SPIs (32–111 fold difference in G') (Table 16).

TABLE 16

Comparisons of the gel-forming properties of BC-SPI, control SPI and commercial SPI. The storage modulus (G') of SPI gels (7% protein, 0.5% NaCl in water phase, pH 5.6) were recorded when the gels were cooled to 20 degrees C (from 70 or 90 degrees C.).

| Protein isolate | 70 C. max G' (Pa) | 90 C. max G' (Pa) |
|---|---|---|
| BC-SPI-acid-ha 90 C. | 2,000 | 4310 |
| Control SPI-acid-ha, 90 C. | 247 | 933 |
| Com'l SPI-D | 25 | 133 |
| Com'l SPI-E | 18 | 65 |

Example 9

Amino Acid and Protein Composition of BC Soybeans

Protein and amino acid compositions of BC soybeans harvested in Jerseryville, Ill. were compared to average composition of 58 diverse lines of soybeans as indicated in Tables 17 and 18. Soybeans (7–10 grams) were finely ground and analyzed for amino acid composition, protein and moisture by Ralston Analytical Laboratories; St. Louis, Mo. according to their standard procedures. The beta-conglycinin rich soybeans had high levels of protein, cysteine, methionine, arginine, and lysine which are especially valued for animal feed and infant formula.

TABLE 17

Showing amino acid and protein content in units of percent, dry basis. The elite line is Hartz 5350.

| Amino acid | Avg. of 58 lines | Range | Elite line | High BC |
|---|---|---|---|---|
| Lysine | 2.42 | 2.11–2.66 | 2.65 | 2.91 |
| Methionine | 0.49 | 0.41–0.57 | 0.55 | 0.62 |
| Cysteine + Met | 1.03 | 0.84–1.19 | 1.14 | 1.44 |
| Threonine | 1.43 | 1.35–1.59 | 1.52 | 1.54 |
| Tryptophan | 0.48 | 0.42–0.55 | 0.50 | 0.48 |
| Arginine | 2.74 | 2.36–3.51 | 2.91 | 3.40 |
| Total protein | 41.0 | 37.4–44.8 | 41.0 | 43.0 |

TABLE 18

Amino acid data for soybeans in units of mg/gram protein:

| Amino acid | Avg. of 58 lines | Range | Elite line | High BC |
|---|---|---|---|---|
| Lysine | 59.6 | 49–66 | 64.6 | 68.0 |
| Methionine | 12.0 | 10.5–13.4 | 13.5 | 14.5 |
| Cysteine + Met | 25.3 | 21–29 | 28.0 | 33.8 |
| Threonine | 35.2 | 30–40 | 37.2 | 36.1 |
| Tryptophan | 11.8 | 10.8–13.0 | 12.1 | 11.1 |
| Arginine | 67.4 | 57–78 | 71.0 | 79.5 |

Example 10

Amino Acid Composition of Soy Protein Isolates

Materials and methods: BC-SPIs, Cntrl-SPI and Com'l SPI-A are described in Example 4. SPIs were analyzed for amino acid composition, protein and moisture by Ralston Analytical Laboratories, St. Louis, Mo. according to their standard procedures.

Results: BC-SPI-acid met the amino acid requirements by the FAO.WHO for 2–5 year olds (Table 19). BC-SPI-acid was not rich in cysteine because much of the cysteine-rich BBI was lost in the whey during processing. The high cysteine composition of BC-SPI-UF is the result of the retention of BBI which is expressed at high levels in high BC soybeans (Example 4).

TABLE 19

Amino acid composition of soy protein isolates

| Amino Acids | Low BC-acid-hb | BC-SPI-acid-hb | BC-SPI-UF-pH7hb | Cntrl-acid-hb | Com'l SPI-A | FAO.-WHO Req. 2–5 yrs old |
|---|---|---|---|---|---|---|
| Cystine (Performic) | | | | | | |
| Cysteine | 12.49 | 12.24 | 18.51 | 12.39 | 11.52 | |
| Methionine | 14.16 | 13.04 | 14.40 | 11.70 | 12.56 | |
| Total sulfur amino acids | 26.64 | 25.29 | 32.91 | 24.08 | 24.08 | 25 |
| Alk Hydrol. Trypt. Amino Acids (Hi Vac) | 14.27 | 11.21 | 10.51 | 11.70 | 11.18 | 11 |
| Aspartic | 124.53 | 119.11 | 117.83 | 114.11 | 111.29 | |
| Glutamic | 204.12 | 203.09 | 191.54 | 204.93 | 195.97 | |
| Alanine | 47.71 | 45.08 | 43.77 | 38.19 | 41.24 | |
| Isoleucine | 48.49 | 47.71 | 44.69 | 41.74 | 42.40 | 28 |
| Phenyl-alanine | 55.52 | 58.58 | 52.91 | 50.92 | 49.19 | |
| Arginine | 76.37 | 77.57 | 74.17 | 74.54 | 71.08 | |
| Threonine | 41.36 | 37.53 | 37.83 | 34.17 | 35.94 | 34 |
| Proline | 55.41 | 51.95 | 53.26 | 51.95 | 50.58 | |
| Valine | 52.95 | 48.97 | 44.80 | 43.69 | 44.59 | 35 |
| Leucine | 86.06 | 90.39 | 81.37 | 77.41 | 78.11 | 66 |
| Histidine | 23.86 | 26.77 | 25.60 | 23.05 | 22.93 | 19 |
| Serine | 53.62 | 55.26 | 54.63 | 50.92 | 49.77 | |
| Glycine | 46.49 | 39.02 | 38.17 | 38.88 | 40.09 | |
| Tyrosine | 41.25 | 39.24 | 38.29 | 35.44 | 37.10 | |
| Lysine | 62.10 | 72.43 | 71.66 | 58.03 | 59.91 | 58 |
| Phe + tyr | 96.77 | 97.83 | 91.20 | 86.35 | 86.29 | 63 |

Amounts are shown in mg/g protein.

Example 11

Physical Properties and Mouthfeel of Processed Cheese Analogs

Materials: BC-SPIs, partially hydrolyzed BC-SPIs and Com'l SPI A are described in Example 4. Com'l SPI G (Supro 710) was from Protein Technologies International, St. Louis, Mo.). Rennet casein was from Century Foods Inc., Sparta, Wis.; soybean oil was from International Food Products, St. Louis, Mo.; sodium citrate dihydrate and lactic acid (80%) from Archer Daniels Midland Company, Decatur, Ill.; Alcalase 2.4 L and Flavourzyme L from Novo Nordisk BioChem North America, Inc., Franklinton, N.C. Stephan UMC 5 cooker (Stephan Machinery Co.) was equiped with a circulating bath (Haake, Paramus, N.J.) containing HF 200 Silicon oil (Haake, Paramus, N.J.).

Cheese melting test: A modified Arnott method was employed. Cheese analog cube samples with controlled dimensions were prepared by a wire cutting device. After preparation, the cheese cubes were placed in air tight plastic bags and stored at 4 degrees C. until testing. The cubes (14×14 mm) were placed on a glass Petri dish, lidded and placed in a 100 degree C. laboratory oven for 15 minutes. The center height of each cube was measured 30 minutes after removal from the oven. The percent length decrease was calculated and is reported as the Arnott meltability on a scale of 0–100.

Cheese texture test: A TAX.T2 Texture Analyzer (Texture Technologies Corp.) was used with a TA-26 cutting wire probe. Cheese cubes (15 mm) were cut and stored in air tight plastic bags at 4 degrees C. Settings: Test mode was to measure force in compression; pretest speed was 1.0 mm/sec.; test speed was 0.5 mm/sec.; post test speed was 5.0 mm/sec.; distance was 90% strain and force was 5 grams.

Moisture test: Two CEM glass fiber pads were fared on the CEM Lab Wave 9000 instrument. Cheese analog (3.5 g.) was spread evenly over a large area of one glass fiber pad. The sample was covered with the remaining glass fiber pad and palced in the instrument for 4 minutes and 30 seconds at 40% power.

Methods for Making Cheese Using Alcalase-Treated BC-SPI:

1. BC-SPI (45–47 g; 30% of the protein in the cheese formula) was added to water (355 g) at 50 degrees C. and mixed thoroughly with a whisk until smooth (55 degrees C.).

2. The pH of the solution was adjusted to 8.0 using 1 N NaOH.

3. Alcalase (0.19 g, 0.51%×g. of protein) was added to the mixture and stirred.

4. The mixture was placed in a Stephan Cooker at approximately 55 degrees C. and mixed at 250 rpm for 45 minutes to allow time for limited hydrolysis of the soy proteins.

5. The mixture was then transferred to a beaker and heated to 90 degrees C. for 7–10 minutes to inactivate the enzyme.

6. The slurry was added to a mixture of sodium citrate, sodium chloride, rennet casein and oil (50 degrees C.) contained in a double boiler.

7. The mass was brought to 66 degrees C. and lactic acid was added (pH of 5.25–5.35) and the mixture was stirred for 4 minutes, the time for the mass to reach 80 degrees C.

8. The hot mass was transferred to a Stephan Cooker (80 degrees C.) and mixed at 250 rpm for 3 minutes and then poured into a plastic container, cooled for 5 minutes, sealed with a lid and stored in a refrigerator (4 degrees C.).

Methods for Making Cheese Using Untreated SPIs

BC-SPI, Com'l SPI A, or Com'l SPI G were also used to make processed cheese analog by mixing the hydrated protein with the other ingredients in the double boiler and following steps 7–8 above.

Methods for Making Cheese Using Flavourzyme:

1. BC-SPI (45 g; 30% of the protein in the cheese formula) and water (300 g.) were added to a beaker of a known weight. The beaker was placed on a tared balance. This weight was recorded as the total weight before hydrolysis.

2. The pH of the solution was not adjusted (pH 6.4).

3. Flavourzyme (0.73 g) was added to the mixture and stirred.

4. The mixture was placed in a Stephan Cooker at approximately 55 degrees C. and mixed at 250 rpm for 90 minutes to allow time for limited hydrolysis of the soy proteins.

5. The mixture was transferred to the beaker in step 1 and heated to 90 degrees C. for 10 minutes and cooled in an ice bath for 10 minutes. The beaker was dried off and placed on the tared balance. The weight was recorded as total weight after hydrolysis.

6. The slurry was added to a mixture of sodium citrate, sodium chloride, rennet casein and oil (50 degrees C.) contained in a double boiler.

7. The mass was brought to 66 degrees C. and the water (total weight before hydrolysis from step 1 minus total weight after hydrolysis from step 5 plus an additional 55 g. of water to compensate for evaporation during cheese making) plus 10 grams of lactic acid (80%) was slowly added to the mixture. The pH was adjusted to 5.25–5.35 with the addition of up to 2 g. of lactic acid (80%).

8. The hot mass was transferred to a Stephan Cooker (80 degrees C.) and mixed at 600 rpm for 4 minutes and then poured into a plastic container, cooled for 5 minutes, sealed with a lid and stored in a refrigerator (4 degrees C.) for 3 days.

The cheeses were 18% protein, 27% fat and 47.5% moisture (Table 20). The moisture levels of the cheeses were higher than commercial product to make it feasible to compare the properties of wider range of soy protein ingredients in the model system, some of which would mix poorly at lower moisture levels.

Results: Cheese analogs containing partially hydrolyzed commercial SPIs (Com'l SPI C & G) and the Alacalase-treated BC-SPI had elastic rather than mealy textures and melted most similar to the cheeses containing only rennet casein as the protein source (Table 21). The Flavourzyme-treated BC-SPI had a smooth and very spreadable texture similar to a cheese spread. This difference in texture was quantified using a compression test (Table 22).

TABLE 20

Cheese analog formula

| Ingredient | Weight grams | Protein grams | Fat grams | Moisture grams |
|---|---|---|---|---|
| Rennet casein (N × 6.38 = 79.9% protein) | 108.0 | 86.29 | | |
| Soy protein (N × 5.71 = protein content) | 45.0 | 35.93 | | |
| Soybean oil | 184.8 | | 184.8 | |
| Sodium citrate | 15.0 | | | |
| Sodium chloride | 10.5 | | | |
| Water | 300.0 (+25–55)* | | | 300.0 |
| Lactic acid (80%) | 10–12 | | | 24 |
| Total | 675.3 | 122.2 | 184.8 | 320.8 |
| Percent of formula | | 18.0 | 27.0 | 47.5 |

*25 or 55 g. added to compensate for water loss by evaporation during cheese making.

TABLE 21

Cheese analog composition, texture and melting properties

| Sample | Texture | pH | Moisture (%) | Melt (%)* |
|---|---|---|---|---|
| Flavourzyme-treated BC-SPI-acid-ha 72 C. | Smooth, spreadable | 5.80 | 47.0 | 57.1 |
| Alacalase-treated BC-SPI-acid-ha 72 C. | Elastic | 5.86 | 47.4 | 50.0 |
| Alacalase-treated BC-SPI-acid-hb 72 C. | Elastic | 5.69 | 46.5 | 50.7 (1.0) |
| BC-SPI-acid-hb | Mealy | 5.89 | 48.2 | 39 (0.8) |
| Com'l SPI A | Mealy | 5.86 | 47.2 | 41 (3.4) |
| Com'l SPI C | Elastic | 5.73 | 46.2 | 55 (2.5) |
| Com'l SPI G | Elastic | 5.92 | 47.7 | 65.5 (1.7) |
| Rennet casein | Elastic | 5.93 | 48.8 | 76.2 |

*% decrease in height of 14 mm high cube heated in 100 degrees C. oven for 15 minutes.
Numbers in brackets show standard deviation for data on two days.

TABLE 22

Texture of cheese analogs as measured by the work necessary for a wire to penetrate the surface and depress into 90% of the cheese samples.

| Soy protein isolate | Area of work (gs) |
|---|---|
| Com'l SPI G | 1389 +/− 131 |
| Com'l SPI C | 1263 +/− 87 |
| Alacalase-treated BC-SPI-acid-ha 72 C. | 1233 +/− 273 |
| Flavourzyme-treated BC-SPI-acid-ha 72 C. | 402 +/− 73 |

Example 12

Low Methionine, High Arginine BC-SPIs as Nutrition and Dietary Supplements

The preparation of new low methionine, high arginine containing BC-SPIs are useful as nutrition and dietary supplements for modulating the total homocysteine level in plasma. Such BC-SPIs are prepared by using conditions which limit disulfide interchange reactions between soy proteins (e.g. by using a reducing agent such as sodium bisulfite) and ultrafiltration to retain beta-conglycinin, glycinin and gamma-conglycinins. The lower molecular weight cysteine and methionine rich proteins pass through the membrane in the permeate. Alternatively a high BC soybean can be developed which is deficient in methionine by selecting appropriate growing conditions, crosses with other soybeans or by modifying the soybean composition. High beta-conglycinin SPI made by an acid precipitation process from high BC soybeans grown in Puerto Rico, was high in arginine (75 mg/g protein) and low in methionine (less than 11 mg/g protein).

Example 13

Reduced Lipoxygenase BC-SPI to Reduce Off-Flavor Development

Lipoxygenase enzymes are known to cause off-flavor development in soy protein ingredients by catalyzing the oxidation of polyunsaturated fats. (Nishiba, Y. et al., J. Agric. Food Chem. 43:738–741, 1995) The lipoxygenase null trait of a soybean variety developed by Keisuke Kitamura (Japan. J. Breed. 41:507–509, 1991) was transferred to a U.S. food bean lacking at least one lipoxygenase genes and then further crossed with the high beta-conglycinin variety to create a low-flavor, high beta-conglycinin soybean variety lacking all three lipoxygenases.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A method for preparing a soy protein composition comprising a beta-conglycinin content greater than 40% of the protein and a glycinin content of less than 10% of the protein, the method comprising:
    a) contacting defatted soybean material and an aqueous solvent to form a mixture of soluble and insoluble components, wherein a portion of the protein is solubilized in the aqueous solvent;
    b) adjusting the pH of the mixture to above approximately 8.5 to increase the portion of the protein solubilized in the aqueous solvent;
    c) removing insoluble components from the mixture;
    d) lowering the pH of the mixture to precipitate a portion of the protein solubilized in the aqueous solvent;
    e) recovering a portion of the protein precipitated in step d.);
    f) adjusting the pH of the protein containing mixture recovered in step e.) to between 6.7 and 7.2; and
    g) drying the mixture.

2. The method of claim 1, further comprising a step of heat-treatment at pH 6.7 to 7.2;
    a) between steps a and b;
    b) between steps c and d;
    c) between steps f and g;
    d) between steps a and b and between steps f and g;
    e) between steps c and d and between steps f and g.

3. The method of claim 2, wherein the heat-treatment step is selected from the group consisting of:
    a) 72–90 degrees C. for 15 to 20 seconds;
    b) 80–90 degrees C. for 5 to 10 minutes; or
    c) 120–154 degrees C. for 7 to 20 seconds.

4. The method of claim 1, wherein the aqueous solvent comprises water.

5. The method of claim 1, wherein the pH of the mixture is adjusted to between 8.5 and 9.5 in step b).

6. The method of claim 1, wherein ratio of soybean material to aqueous solvent is 1 to 10.

7. The method of claim 1, further comprising the step of mixing the soybean material and the aqueous solvent with an agitator.

8. The method of claim 1, wherein the insoluble components are removed from the mixture by centrifugation.

9. The method of claim 1, wherein the pH in step d) is between 4.4 and 4.6.

10. The method of claim 1, wherein the portion of the precipitated protein is recovered in step e) using a desludging disk centrifuge.

11. The method of claim 2, wherein the heat-treatment step is 72–90 degrees C. for 15 to 20 seconds.

12. The method of claim 2, wherein the heat-treatment step is 80–90 degrees C. for 5 to 10 minutes.

13. The method of claim 2, wherein the heat-treatment step is 90–154 degrees C. for up to 20 seconds.

* * * * *

UNITED STATES PATENT AND TRADEMARK OFFICE
CERTIFICATE OF CORRECTION

PATENT NO. : 6,566,134 B2  
DATED : May 20, 2003  
INVENTOR(S) : Bringe

It is certified that error appears in the above-identified patent and that said Letters Patent is hereby corrected as shown below:

Column 38,
Line 33, please delete "or" and insert -- and -- therefor.

Signed and Sealed this

Twenty-third Day of September, 2003

JAMES E. ROGAN
*Director of the United States Patent and Trademark Office*